(12) United States Patent
Carron et al.

(10) Patent No.: US 10,072,984 B2
(45) Date of Patent: Sep. 11, 2018

(54) SPECTROMETER

(71) Applicant: MKS TECHNOLOGY, Centennial, WY (US)

(72) Inventors: Keith T. Carron, Centennial, WY (US); Shane A. Buller, Laramie, WY (US); Mark A. Watson, Laramie, WY (US); Sean Patrick Woodward, Laramie, WY (US)

(73) Assignee: MKS Technology, Inc., Centennial, WY (US)

( * ) Notice: Subject to any disclaimer, the term of this patent is extended or adjusted under 35 U.S.C. 154(b) by 0 days.

(21) Appl. No.: 14/874,378

(22) Filed: Oct. 2, 2015

(65) Prior Publication Data
US 2016/0223400 A1    Aug. 4, 2016

Related U.S. Application Data

(60) Provisional application No. 62/058,926, filed on Oct. 2, 2014, provisional application No. 62/192,023, filed
(Continued)

(51) Int. Cl.
*G01J 3/44*    (2006.01)
*G01N 21/65*    (2006.01)
(Continued)

(52) U.S. Cl.
CPC .............. *G01J 3/4412* (2013.01); *G01J 3/021* (2013.01); *G01J 3/027* (2013.01); *G01J 3/0208* (2013.01);
(Continued)

(58) Field of Classification Search
CPC ....................................................... G01J 3/4412
(Continued)

(56) References Cited

U.S. PATENT DOCUMENTS 5,070,246 A    12/1991  Durham et al.
5,807,750 A    9/1998   Baum et al.
(Continued)

OTHER PUBLICATIONS

ISA/US International Search Report and Written Opinion dated Jan. 22, 2016 in reference to co-pending International Application No. PCT/US2015/053887 filed Oct. 2, 2015.

*Primary Examiner* — Tarifur Chowdhury
*Assistant Examiner* — Omar Nixon
(74) *Attorney, Agent, or Firm* — Dinsmore & Shohl LLP; Thomas J. Osborne, Jr.

(57) ABSTRACT

Spectrometers and methods for determining the presence or absence of a material in proximity to and/or combined with another material are provided. In one particular example, a spectrometer is provided that includes a light source, a detector and an optical system. In this implementation, the light source is configured to provide an excitation incident beam. The detector is configured to detect a spectroscopy signal. The optical system is configured to direct the excitation incident beam toward a sample at a non-zero angle from a zero-angle reference. The optical system is further configured to receive a spectroscopy signal from the sample and provide the spectroscopy signal to the detector. The detector is configured to remove a spectral interference component of the spectroscopy signal.

21 Claims, 29 Drawing Sheets

Related U.S. Application Data on Jul. 13, 2015, provisional application No. 62/234,522, filed on Sep. 29, 2015.

(51) Int. Cl.
*G01J 3/02* (2006.01)
*G01J 3/10* (2006.01)
*G01N 21/47* (2006.01)

(52) U.S. Cl.
CPC ............... *G01J 3/0297* (2013.01); *G01J 3/10* (2013.01); *G01J 3/44* (2013.01); *G01N 21/65* (2013.01); *G01N 2021/4711* (2013.01); *G01N 2201/068* (2013.01); *G01N 2201/0612* (2013.01); *G01N 2201/12* (2013.01)

(58) Field of Classification Search
USPC ........................................................ 356/317
See application file for complete search history.

(56) References Cited

U.S. PATENT DOCUMENTS

| | | |
|---|---|---|
| 7,542,140 B2 | 6/2009 | Ouchi et al. |
| 7,911,604 B2 | 3/2011 | Matousek et al. |
| 8,009,288 B2 | 8/2011 | Berlin et al. |
| 8,264,680 B2 * | 9/2012 | Tanaami ............ G01N 21/6428 250/458.1 |
| 8,743,358 B2 | 6/2014 | Treado et al. |
| 2005/0248758 A1 * | 11/2005 | Carron ...................... G01J 3/02 356/301 |
| 2010/0195108 A1 | 8/2010 | Prystupa |
| 2012/0127467 A1 * | 5/2012 | Ivanov ............... G01N 21/6408 356/326 |
| 2012/0274934 A1 * | 11/2012 | Messerschmidt ...... G01N 21/65 356/301 |
| 2014/0016127 A1 * | 1/2014 | Yamazoe ............. G01N 21/658 356/301 |

* cited by examiner

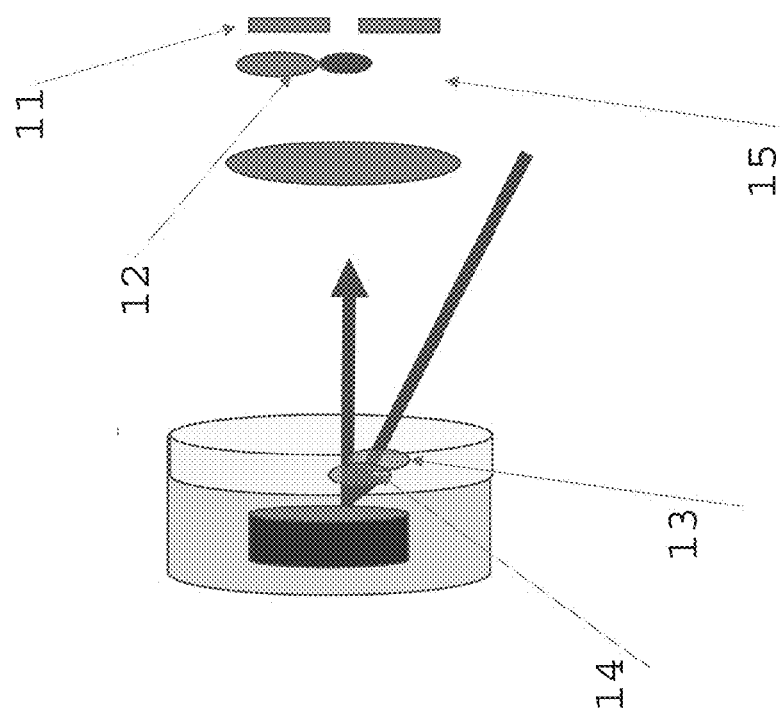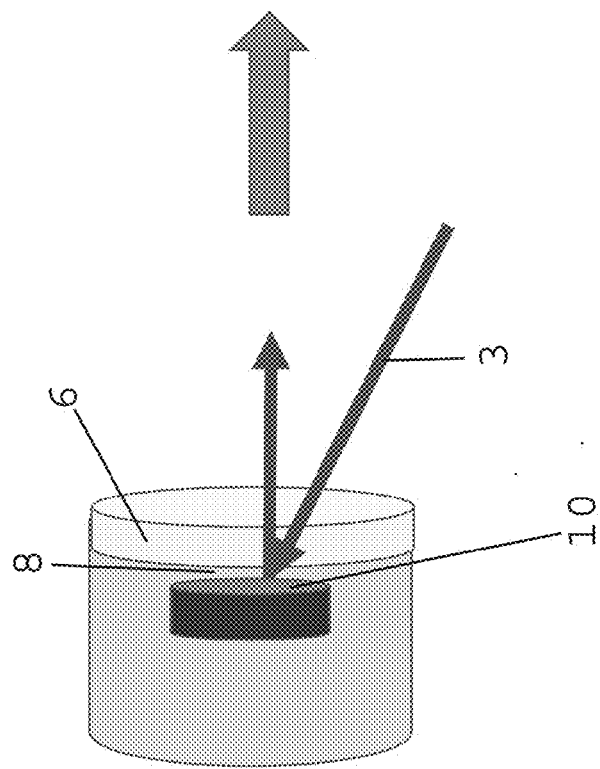
FIGURE 4

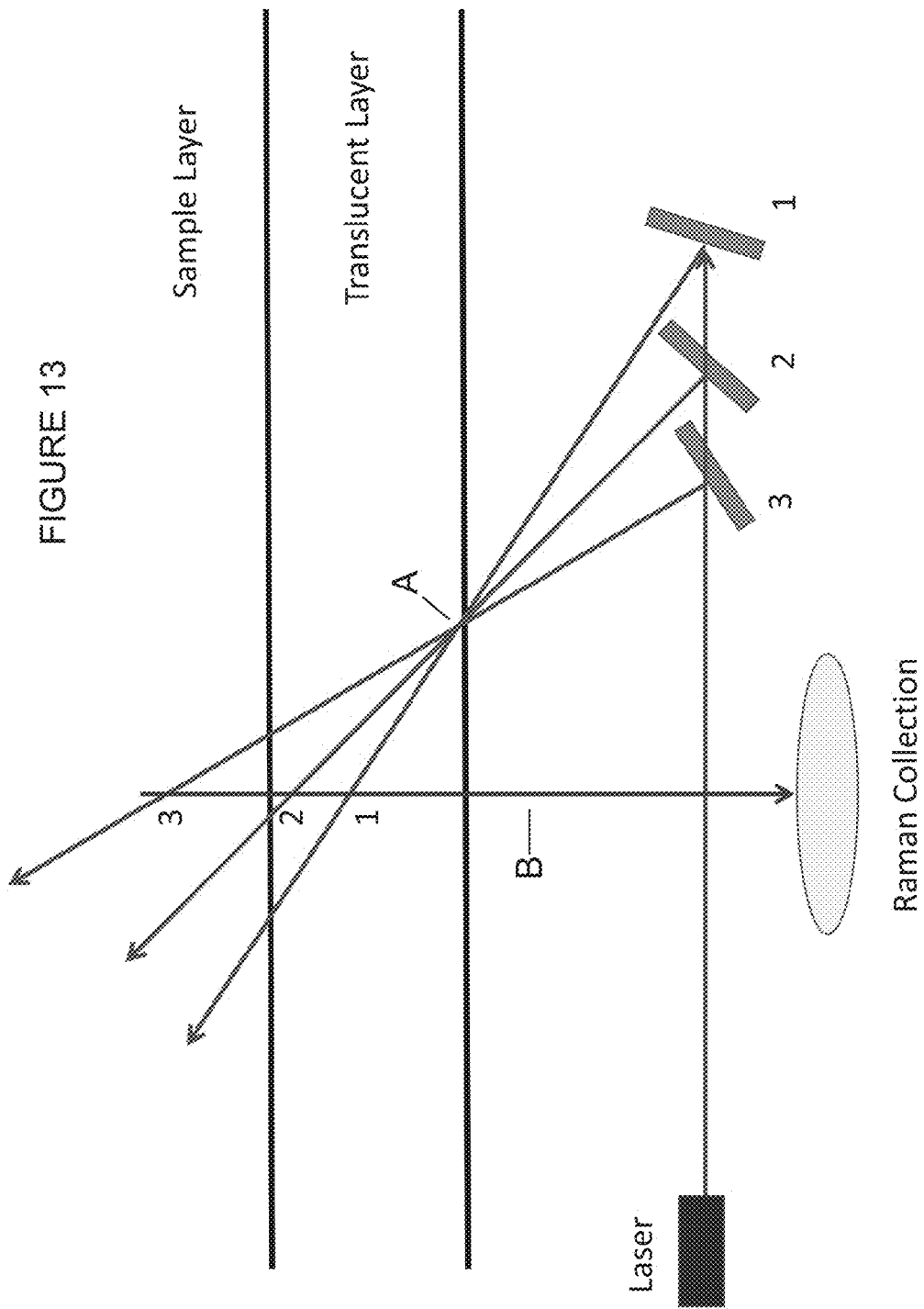

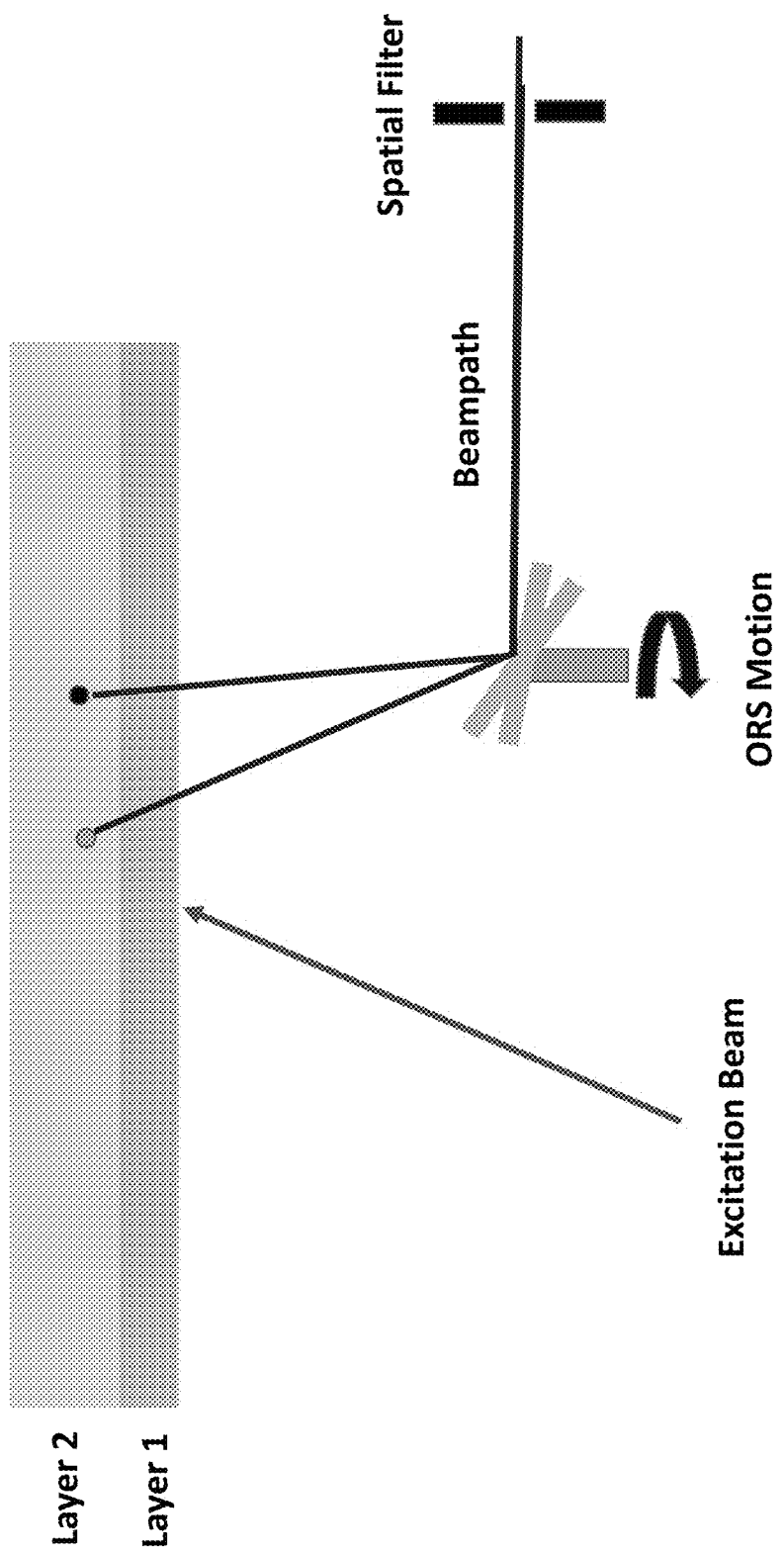

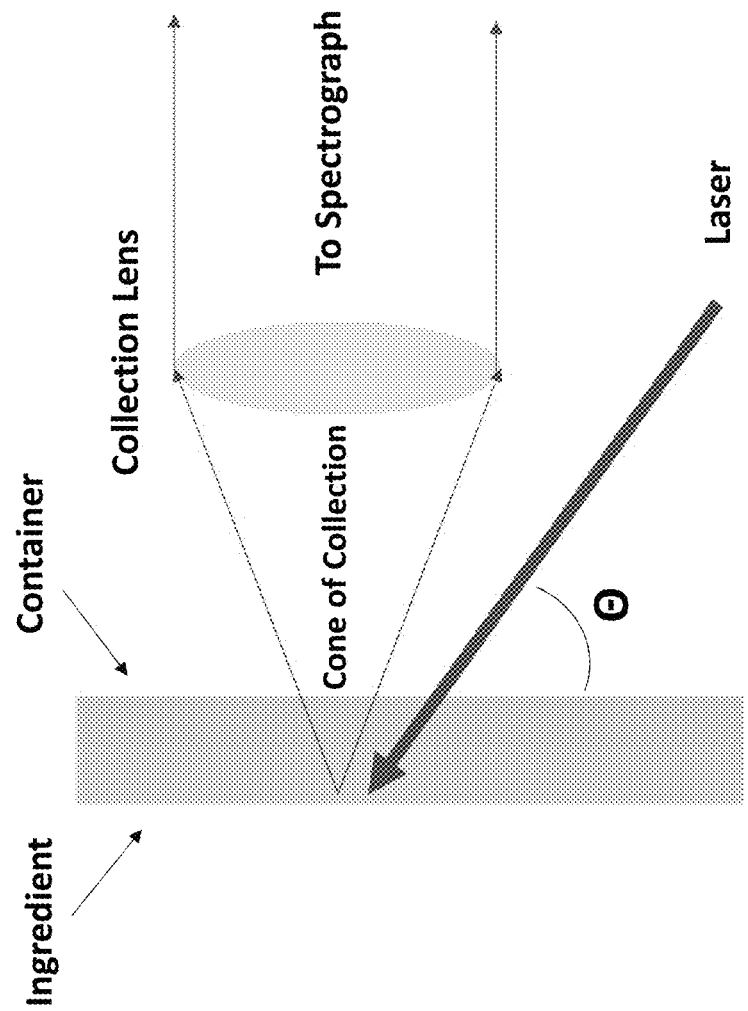

SPECTROMETER

CROSS-REFERENCE TO RELATED APPLICATIONS

This application claims the benefit of U.S. provisional application Nos. 62/058,926, filed Oct. 2, 2014, 62/192,023 filed Jul. 13, 2015 and 62/234,522 filed Sep. 29, 2015. Each of the provisional patent applications is hereby incorporated by reference, including all appendices, as though fully set forth herein.

BACKGROUND

Field

The instant invention relates to spectrometers configured to reduce interference caused by a material disposed adjacent (directly or indirectly adjacent) and/or proximate (e.g., in close proximity) to a sample of interest.

Background

It is well known that Raman spectroscopy can be performed at angles other than zero degrees. The popular zero degree method, also known as epi-illumination, has advantages with regard to alignment. For example, the method described by Carron et al. in U.S. Pat. No. 7,403,281 entitled "Raman Spectrometer," which is hereby incorporated by reference in its entirety as if fully set forth herein, describes an epi-illumination scheme in which a system operator does not need to align the laser excitation at the sample with the collection optics and small aperture. This is possible because the manufacturer pre-aligns the beams with a beam splitter.

While this approach is creates an easy to use method for Raman spectroscopy it can also create a problem when an illumination beam of a spectrometer passes through a different material to illuminate a sample. This may create a region of interference 2 as illustrated in FIG. 1. The interference may arise from a container material and/or a material between the container surface and the desired sample. Dr. Carron in his PhD dissertation, Surface Enhanced Resonance Raman, Resonance Hyper-Raman, and Hyper Raman spectroscopy of Molecules Absorbed to Thin Metal Films (1985, Northwestern University), describes a method of providing an excitation signal 3 at an angle 4 to eliminate and/or reduce the region of interference 2 shown in FIG. 1. FIG. 2, taken from Carron's dissertation (page 151), illustrates this method. The approach removed Raman scattering from a window material 6 or solution 8 prior to the sample of interest 10.

FIG. 3 and FIG. 4 illustrate in detail the advantage of the off-axis method used by Carron (1985). In FIG. 3, for example an excitation signal 3 is directed toward a sample 10 at an off-axis angle 4 by a mirror 12. The excitation signal 3 travels through a window material 6 and a solution 8 to the sample 10. FIG. 4 illustrates how a spatial filter 11 of a disperse Raman system may be used to remove interference 12, collectively corresponding to interference 13 from a window 6 and interference 14 from another material, such as the solution 8, disposed prior to the sample 10. The spatial filter 11, in contrast, passes an image/Raman scattering 15 corresponding to the sample 10 to a detector. Raman scattering from other materials (e.g., the window 6 and/or solution 8) or other interference such as fluorescence can be removed by the spatial filter 11.

BRIEF SUMMARY

Spectrometers and methods for determining the presence or absence of a material in proximity to and/or combined with another material are provided. In one particular example, a spectrometer is provided that includes a light source, a detector and an optical system. In this implementation, the light source is configured to provide an excitation incident beam. The detector is configured to detect a spectroscopy signal. The optical system is configured to direct the excitation incident beam toward a sample at a non-zero angle from a zero-angle reference. The optical system is further configured to receive a spectroscopy signal from the sample and provide the spectroscopy signal to the detector. The detector is configured to remove a spectral interference component of the spectroscopy signal.

In other implementations, spectrometers and methods for determining the presence or absence of a material in proximity to and/or combined with another material are also provided. In this implementation, the spectrometer includes a light source, a detector and an optical system. The light source is configured to provide an excitation incident beam. The detector is configured to detect a spectroscopy signal. The optical system is configured to direct the excitation incident beam toward a sample at a non-zero angle from a zero-axis reference, receive a spectroscopy signal from the sample and provide the spectroscopy signal to the detector. The detector is further configured to compare a plurality of spectroscopy signals corresponding to a plurality of incident beams directed toward the sample from a plurality of different non-zero angles and/or offsets from the zero-axis reference to identify at least one component of the spectroscopy signal corresponding to the sample.

In other implementations, further spectrometers and methods for determining the presence or absence of a material in proximity to and/or combined with another material are also provided. In one implementation, for example, a system or method provide for measuring Raman scattering from layers within a sample. The system and method excite Raman scattering at a nonzero angle relative to a normal angle of incidence relative to the sample. The system and method also use multiple angles to interrogate the different depths within the sample and collect Raman spectra at the normal angle of incidence to the surface; and using statistical methods to derive the different layers within the sample.

In yet other implementations, spectrometers and methods for determining the presence or absence of a material in proximity to and/or combined with another material are also provided. In one implementation, for example, a system and method of measuring Raman scattering from layers within a sample excite Raman scattering by directing an excitation beam toward the sample at a nonzero angle relative to a normal angle of incidence relative to the sample; translate the using multiple angles to interrogate the different depths within the sample; collect Raman spectra at normal incidence to the surface; and use statistical methods to derive the different layers within the sample.

In yet other implementations, spectrometers and methods for determining the presence or absence of a material in proximity to and/or combined with another material are also provided. In one implementation, for example, a system and method of measuring Raman scattering from layers within a sample excite Raman scattering at a nonzero angle relative to a normal angle of incidence relative to the sample; collect collecting Raman spectra at the normal angle of incidence to the surface; collect a spectrum of a first layer without ingredients; collect a spectrum of the first layer and a second layer; and determine a spectrum of the second layer through normalization against the spectrum of the first layer.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 4 depicts an example of the method of FIG. 2.

FIG. 13 depicts an example implementation of a spectrometer in which the optical system of the spectrometer includes separate excitation and collection optical paths.

FIG. 18 depicts another example implementation of a method of using subtraction of a normalized standard deviation from an average to produce a spectrum of a second layer.

FIG. 26 depicts an example implementation of a spectroscopic system in which an excitation beam is fixed at an angle to a surface of a multi-layered sample.

FIG. 27 depicts an example implementation of a method to identify a material through a barrier, such as a container.

DETAILED DESCRIPTION

A spectrometer (e.g., a Raman or luminescence (e.g., fluorescence, phosphorescence, chemilluminescence) spectrometer) is provided that reduces interference caused by a material disposed adjacent (directly or indirectly adjacent) and/or proximate (e.g., in close proximity) to a sample of interest. In various implementations, the material causing interference with a spectroscopy signal of a sample of interest may include a container (e.g., a test tube, plastic container, etc.) or another material located proximate (e.g., in close proximity) to the sample of interest. Although particular types of spectrometers are described below (e.g., Raman and fluorescent), these are merely examples of spectrometers that may be used in a similar manner to reduce interference in a spectroscopy signal.

Figure 1:
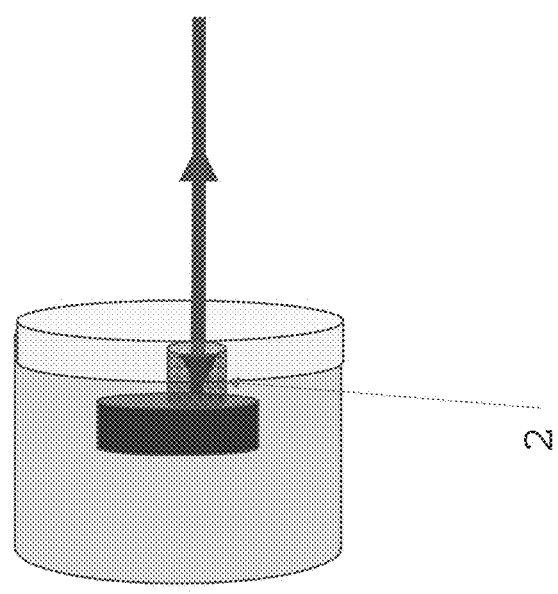
FIG. 1 depicts an example of a region of interference in a spectroscopy application due to epi-illumination.
Figure 2:
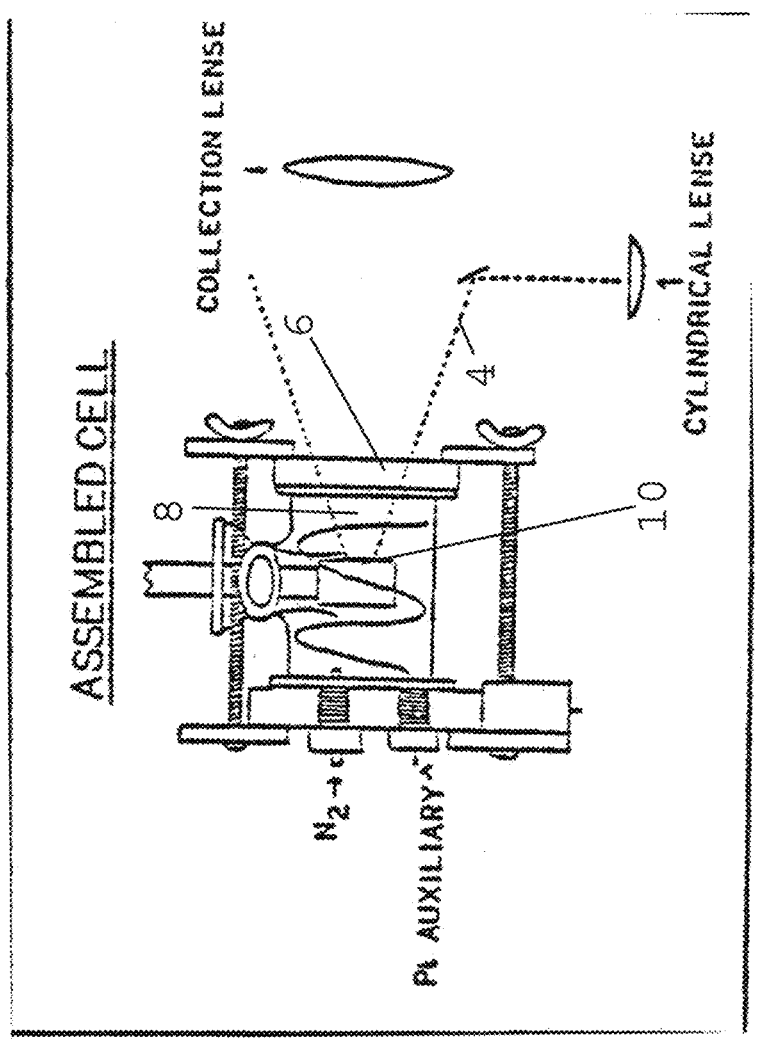
FIG. 2 depicts an example method of providing an excitation signal at an angle to eliminate and/or reduce the region of interference shown in FIG. 1.
Figure 3:
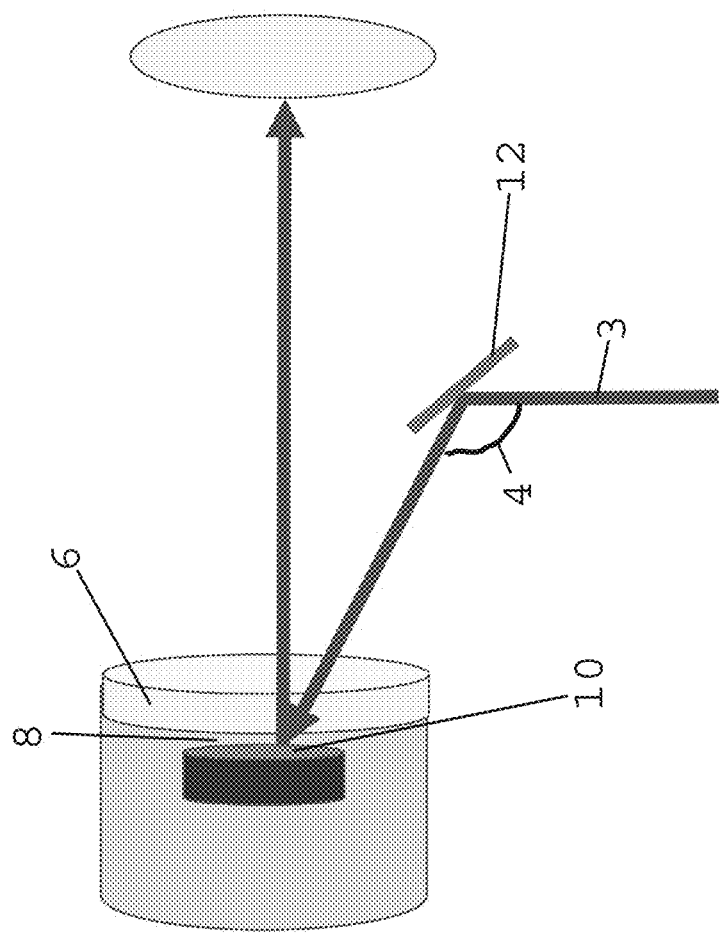
FIG. 3 depicts an example of the method of FIG. 2.
Figure 5:
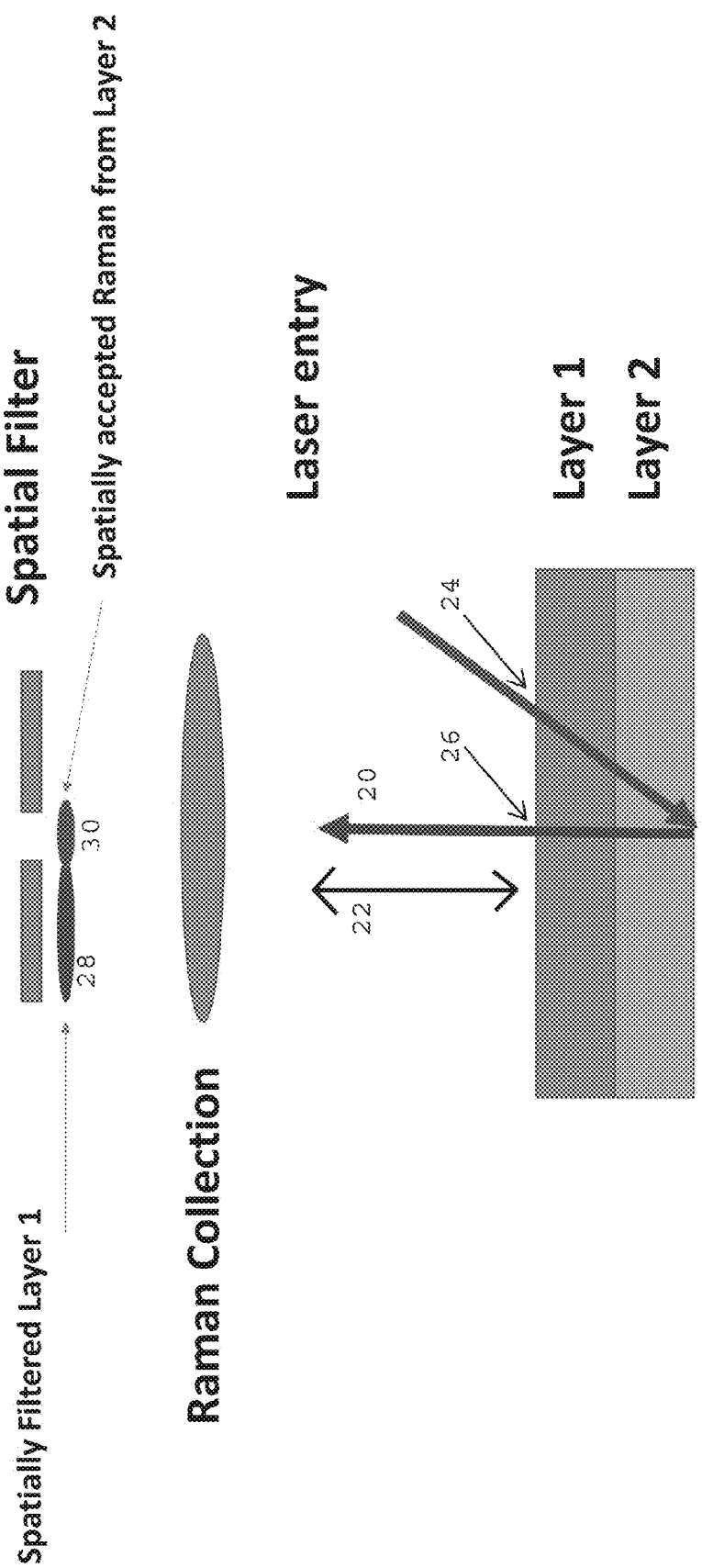
FIG. 5 depicts example implementation of a Raman system including a non-zero angle excitation beam configured to excite first and second layers of a sample.

FIG. 5 illustrates an example implementation of a Raman system including a non-zero angle excitation beam configured to excite first and second layers of a sample. The first and second layers may comprise individual layers of a sample, or may correspond to a container or window (first layer) that is disposed in front of a target sample (second layer). In addition, the first and second layers may be directly adjacent to each other or positioned such that one or more additional layers may be disposed between the first and second layer and/or in front of/behind the first and second layers relative to a spectrometer.

In the particular implementation shown in FIG. 5, for example, the excitation beam is directed toward the first layer at a non-zero angle (i.e., a non-zero angle from a line 20 generally perpendicular to the sample) from a collection axis 22. The excitation beam is directed toward an entry region 24 on a surface of the first layer. The entry region 24 is offset from a collection region 26 by a distance d. The excitation beam disperses through the first layer to the second layer. Although in the particular example shown in FIG. 5 the excitation beam is shown reaching and exciting the second layer at a position generally perpendicular within the sample to the collection region 26 at a surface of the sample, the excitation beam need not be directed so that would intersect the zero-axis line 20 within the second layer at the position generally perpendicular within the sample to the collection region. Rather, the excitation beam is generally directed at a non-zero angle toward the zero-axis line 20 so that intersections with the first and second layers correspond to generally different distances from the collection region 26 as the excitation beam disperses through the first and second layers of the sample. In one implementation, for example, the excitation beam may be shifted left or right from the position shown in FIG. 5 and intersect or not intersect the zero-angle line 20 corresponding to the collection region 26.

In the particular implementation shown in FIG. 5, for example, the excitation beam enters the first layer of the sample and excites the first layer at an excitation region offset a distance from a collection region of the sample. The excitation beam also excites the second layer of the sample at or closer to the collection region of the sample than the excitation region of the first layer of the sample. A spatial filter of a spectrometer is configured to spatially filter all or a portion of a spectrometer signal corresponding to the first layer of the sample at point 28 and to spatially accept or passed to a detector of the spectrometer all or a portion of the spectrometer signal corresponding to the second layer of the sample at point 30.

Further, depending on the angle of the excitation beam with respect to the zero-axis line, more or less relative contributions of the first and second layers may be achieved. In the particular example shown in FIG. 5 where the excitation beam is directed toward the collection region 26 and zero-axis line 20, for example, a relatively lesser angle of the excitation beam with respect to the zero-axis line 20 corresponds to an excitation of the first layer at a relatively closer distance to the collection region while a relatively larger angle of the excitation beam with respect to the zero-axis line 20 corresponds to an excitation of the first layer at a relatively further distance to the collection region. Where the excitation of the first layer is closer to the collection region (lesser angle in this example), the relative contribution of the first layer to the signal collected by the spectrometer via the spatial filter is greater than where the excitation of the first layer is further to the collection region (greater angle in this example).

Figure 6:
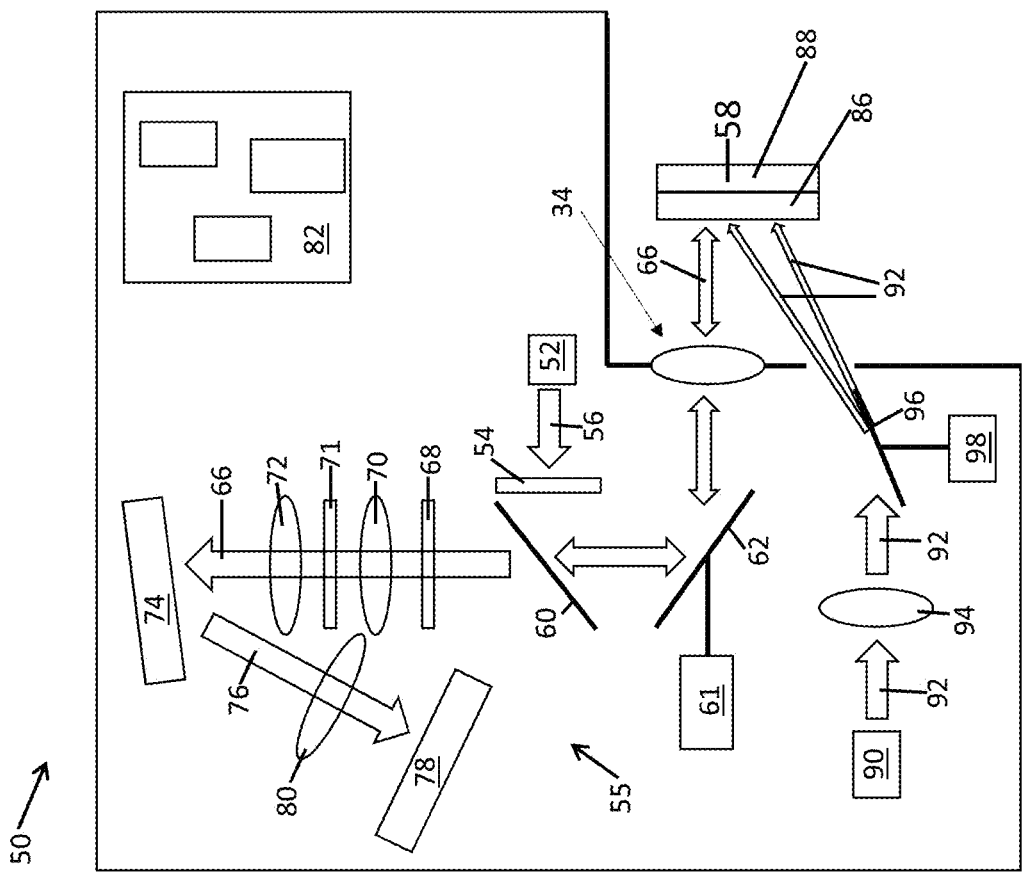
FIG. 6 depicts an example implementation of a spectrometer configured to reduce interference caused by a material disposed adjacent (directly or indirectly) to a sample of interest.

FIG. 6 shows an example implementation of a spectrometer 50 configured to reduce interference caused by a material 86 disposed adjacent (directly or indirectly) to a sample 88 of interest. In one implementation, for example, the material 86 may correspond to the first layer and the sample 88 may correspond to the second layer of the sample shown in FIG. 5. Although the particular example shows a Raman spectrometer, other types of spectrometers, such as a luminescence spectrometer, could readily be designed based on the description herein. As shown in FIG. 6, the spectrometer 50 comprises an excitation source 52 configured to generate an excitation incident beam 56. In a Raman spectrometer, for example, the excitation source 52 typically comprises a laser light source. In one implementation, for example, the excitation source 52 comprises a diode laser. A diode laser, for example, is capable of providing a plurality of wavelengths from the excitation source 52. The spectrometer 50 further comprises a filter 54. The filter 54 filters the output of the excitation source 52, such as removing spurious emissions from the excitation source 52.

The spectrometer 50 further comprises an optical system 55. The optical system 55 directs the incident beam 56 toward a sample 58 and receives a spectroscopy signal from the sample 58. In the implementation shown in FIG. 6, for example, the optical system 55 comprises a dichroic beamsplitter mirror 60. However, the incident beam 56 may be directed at sample 58 without any intervening instrument components located in the path of incident beam 56. The incident beam 56 also may be directed at a mirror, a holographic transmissive element, a mirror formed with a hole in the mirror or any other means for directing an incident beam known in the art.

In this particular implementation, the optical system 55 further comprises one or more optical elements configured to deliver the incident beam to the sample 58 and direct/move the beam with respect to a surface of the sample 58. In the particular implementation shown in FIG. 6, for example, the optical system 55 further comprises an actuator 61 (e.g., an actuator motor) and a movable mirror 62 or other optical element to reflect or otherwise direct and move the incident beam 56 across a surface of the sample 58. Various implementations of optical systems and methods for moving an incident beam relative to a surface of a sample are shown and described in U.S. Pat. No. 8,988,678 entitled "Spectrometer," filed on Aug. 31, 2011 and issued on Mar. 24, 2015 and U.S. patent application Ser. No. 13/907,812 entitled "Spectrometer" and filed on May 31, 2013, each of which is incorporated by reference as if fully set forth herein. In one implementation, for example, an actuator assembly 61 moves (e.g., displaces and/or angles) one or more element of the optical system 25 (e.g., a moveable mirror 62) to move the beam with respect to a surface of the sample 58 (e.g., move the beam across a surface of the sample 58). The actuator assembly 61, for example, may control a displacement and/or angle of the moveable mirror 62 to direct the incident beam in toward the sample 58.

The incident beam 56 may further be directed through a lens 64. In one implementation, the lens 64 comprises a focusing lens in the path of the incident beam 56. The focusing lens couples the incident beam 56 with the sample 58 and collects a spectroscopy signal (e.g., Raman scattered light) from the sample. In another implementation, more than one lens 64 may be located in the path of the incident beam 56 before the incident beam 56 is directed toward the sample 58 from the moveable mirror. In various implementations, the spectrometer 50 may include other optical elements for directing an incident beam 56 toward a sample and collecting a spectroscopy signal from the sample. The optical system of the spectrometer 50, for example, may include elements such as a collimated beam tube or a fiber optic waveguide. See, e.g., U.S. Pat. No. 7,403,281 for examples of collimated beam tubes or fiber optic waveguides that may be used in optical systems of various spectrometers.

In the particular implementation shown in FIG. 6, for example, an offset excitation source 90 generates an offset excitation incident beam 92. The offset excitation source 90, for example, may also comprise a laser light source, diode laser light source or other spectrometer light source. A focusing lens 94, for example, focuses the excitation incident beam 92 and directs the beam 92 towards an offset mirror 96. The offset mirror 96 (or other optical element configured to direct the incident beam) may be fixed to deliver the incident beam 92 at an angle (e.g., a predetermined angle) toward the sample 58 from an offset direction. In another implementation, for example, the offset mirror 96 (or other optical element configured to direct the incident beam) may be movable so that the incident beam 92 may be directed toward the sample 58 at one or more different angles and/or may be movable so as to move the beam relative to a surface of the sample 58 as described above with respect to mirror 62. An actuator 98, such as a motor, may be configured to move the mirror 62 (or other optical element).

In one implementation, for example, the mirror 96 and/or the actuator 98 may be configured to direct the excitation incident beam 92 towards the sample 58 at one or more non-zero angles relative to a collection axis (generally coincident with spectroscopy signal 66 shown in FIG. 6 and as further described and shown with respect to FIG. 5 above). The actuator assembly 98, for example, may control a displacement and/or angle of the moveable mirror 96 (or other optical element) to direct the incident beam 92 toward the sample 58.

The incident beams 56, 92 induce or generate on contact with the sample 58 a spectroscopy signal to be detected by the spectrometer 50. In Raman spectroscopy, for example, the incident beam 56 induces or generates on contact with the sample 58 scattered radiation having an energy differential different from, and one or more wavelengths different than, the incident radiation 56, 92, or the Raman shift that, for convenience, may be described as a Raman beam. As stated above, and as shown in FIG. 6, in one implementation, the spectrometer 50 comprises a beam-splitter, such as a dichroic beam-splitter mirror 60. The spectroscopy signal 66 (e.g., Raman beam) is directed back through the lens 64 and the dichroic beam-splitter mirror 60. Neither the incident beams 56, 92 nor the spectroscopy signal 66 need be co-linear. In the implementation shown in FIG. 6, however, the spectroscopy signal 66 passes back through the dichroic beam-splitter mirror 60 and then through a filter element 68. In one implementation, the filter element 68 comprises a long pass filter that removes extraneous radiation (e.g., from the light source 52 or another source) prior to dispersing the spectroscopy signal 66 into a spectrum. Alternatively, the filter element 68 may comprise a notch filter, or any other filter that is capable of rejecting elastically scattered radiation.

The spectroscopy signal 66 may further pass through an input focusing lens 70 that focuses the spectroscopy signal 66 to a point at a spatial filter 71. In one implementation, for example, the spatial filter 71 comprises an aperture, slit or notch and is located at the focal point of the input focusing lens 70. The spatial filter 71 spatially filters the beam at the focal point of the input focusing lens.

The spectrometer 50 shown in FIG. 6 further comprises a collimating lens 72 that collimates the diverging spectroscopy signal 66 after it has passed through an aperture of the spatial filter 71 (e.g., an aperture, slit or notch). The collimating lens 72 further directs the re-collimated Raman beam toward a diffraction grating 74. The diffraction grating 74 comprises an optical element that divides a Raman beam into spatial separated wavelengths. The diffraction grating 74 further directs a divided Raman beam 76 toward a detector 78. The divided Raman beam 76 passes through a detector focusing lens 80 that focuses the spatially separated wavelengths of the divided Raman beam 76 onto the detector 78.

The detector 78 comprises a transducer that converts optical energy into an electrical signal. In one implementation, for example, the detector 78 comprises an array of individual transducers that create an electrical pattern representing the spatially separated wavelengths of the Raman spectrum. A charge-coupled device (CCD) array, for example, may be used as the detector 48 in one implementation of the invention. In another implementation, an Indium-Gallium-Arsenide (InGaAs) detector 78. Other detectors known in the art may also be used within a spectrometer of the present invention.

The spectrometer 50 further comprises control electronics 82 for controlling the operation of the spectrometer 50. The control electronics 82, for example, may control the operation of the light sources 52, 90, the actuator assemblies 61, 98 the detector 78, temperature control elements (e.g., for the light source or detector), and data transfer to and/or from the spectrometer. In one implementation, the control electronics 82 may be integrated onto a single PC board within a housing of the spectrometer. The control electronics 82 may also comprise one or more discrete component(s) and/or one or more integrated circuit component(s).

In one implementation, the control electronics 82 may comprise a means for communicating with an external device. The means for communicating, for example, the means form communicating may comprise a wired or wireless communication port for communicating with an external computer, personal data assistant (PDA), network or the like. A wired communication port, for example, may comprise a parallel, serial, universal serial bus (USB), FireWire™, IEEE 1394, Ethernet, modem, cable modem or other wired communication port known in the art. A wireless communication port, for example, may comprise an antenna for wireless communicating with an external device, such as via and infrared, Bluetooth, IEEE 802.11a/b/g, IrDA, a wireless modem or other wireless communication port known in the art. The control electronics 82 may be powered from a battery for a portable device or may include a power input for receiving power from an external supply as known in the art. A battery or power supply circuit (e.g., a rectifier) may be located within a housing of the spectrometer 50.

In Raman spectroscopy, the spectrometer 50 operates to detect a Raman spectrum of a sample 58. In order to detect the Raman spectrum, the light source 52, 90 is activated to generate an incident beam 56, 92 of excitation radiation, such as generating a laser incident beam in a laser light source. In one implementation, for example, the temperature of the light source 52, 90 is controlled to control the output frequency of the incident beam 56 generated by the light source 52, 90. The incident beam 56, 92 of excitation radiation may pass through the filter 54, which removes spurious emissions from the incident beam. The incident beam 56 is reflected off the beam-splitter mirror 60 toward the sample 58. The incident beam 56 is focused onto the sample 58 by the output focusing lens 64.

The incident beam 56 generates Raman scattered light from the sample 58. The Raman scattered light is received by the output focusing lens 64 and transmitted back through the beam-splitter mirror 60. In this implementation, the beam-splitter mirror 60 passes the Raman scattered light through the mirror 60 to the filter 68. From the filter 68, the Raman scattered light passes through the input focusing lens 70 and is focused onto a spatial filter 71 such as an aperture, slit or notch. The Raman scattered light is spatially filtered and diverges toward the collimating lens 72. The collimating lens 72 collimates the diverging Raman scattered light and transmits the light to the diffraction grating 74, which divides the Raman scattered light into spatial separated wavelengths and directs the wavelengths towards the detector element 78. The spatially separated wavelengths of the Raman scattered light pass through the detector focusing lens 80 and are focused into a focused band of radiation that represents the spatially separated wavelengths of the Raman scattered light. The focused band of radiation is further directed by the detector focusing lens 80 onto the detector 78.

In this particular implementation, the detector 78 comprises an array of individual transducers that each generate an electrical signal corresponding to intensity of the radiation received at each of the individual transducers. The electrical signals generated at the individual transducers of the detector represent the spatially separated wavelengths of the Raman spectrum of the sample 58. The electrical signals are read from the detector by the control electronics 82. In one implementation, for example, the spectrometer 50 may then present the Raman spectrum detected to a user such as via a display or indicator on the spectrometer itself. In another implementation, the control electronics of the spectrometer 50 may comprise a look-up table stored in a data storage element (e.g., memory, tape or disk drive, memory stick or the like). In this implementation, the control electronics 82 compares the signal from the detector with the values stored in the look-up table to determine a result of the Raman scan. The spectrometer 50 then presents the result to a user such as via a display or indicator on the spectrometer. The result, for example, may indicate the presence or absence of one or more chemicals or substances in the sample and may further indicate an amount or concentration of a chemical or substance detected by the spectrometer.

In other implementations, the detector 78 may comprise one or more individual transducers that rapidly scan for one or more anticipated spectral features (e.g., Raman features). An example such system is disclosed in U.S. patent application Ser. No. 13/161,485 entitled "Spectrometer" and filed by Carron et al. on Jun. 15, 2011, which is hereby incorporated herein by reference in its entirety for all that it teaches and suggests.

Figure 7:
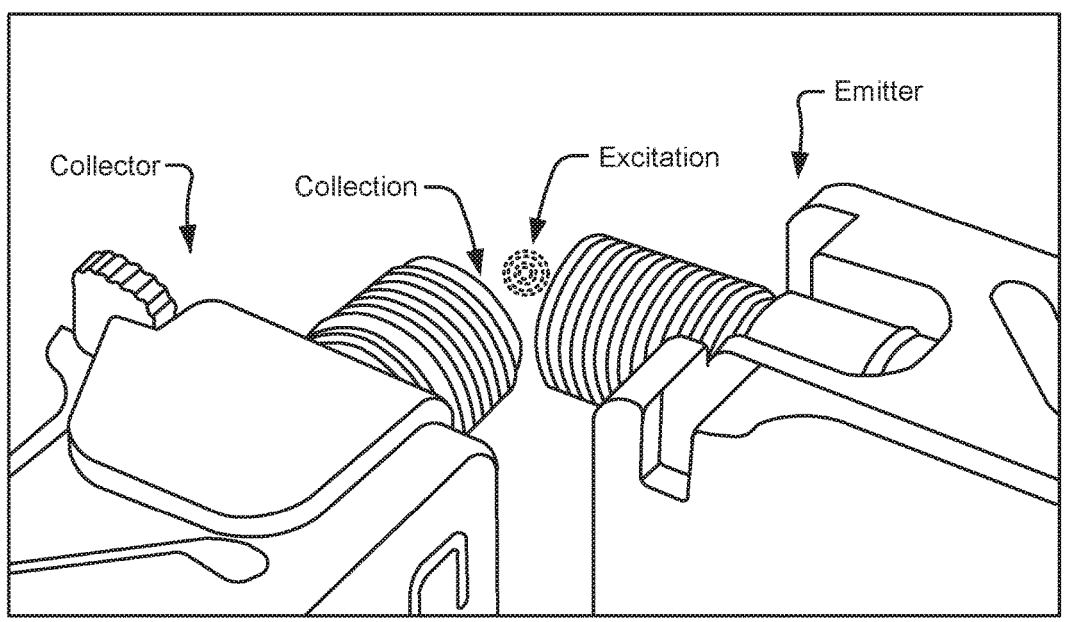
FIG. 7 depicts an example system configured to examine layers of a sample.

FIG. 7 illustrates an experimental design which examines to layers of a sample (e.g., Delrin and Teflon of a plastic material). In this example implementation, a first system emits laser excitation incident beam while the other collects Raman scattered light with a spatially filter collection. In this case, a delineation between a first layer (e.g., Teflon) and a second layer (e.g., Delrin) is continuous and even at a fairly large angle the spectrum contains signals from both layers. If a spectral library of material is searched then it is possible to remove the interference through spectral subtraction or other mathematical approaches such as, but not limited to, principal component analysis.

Figure 8:
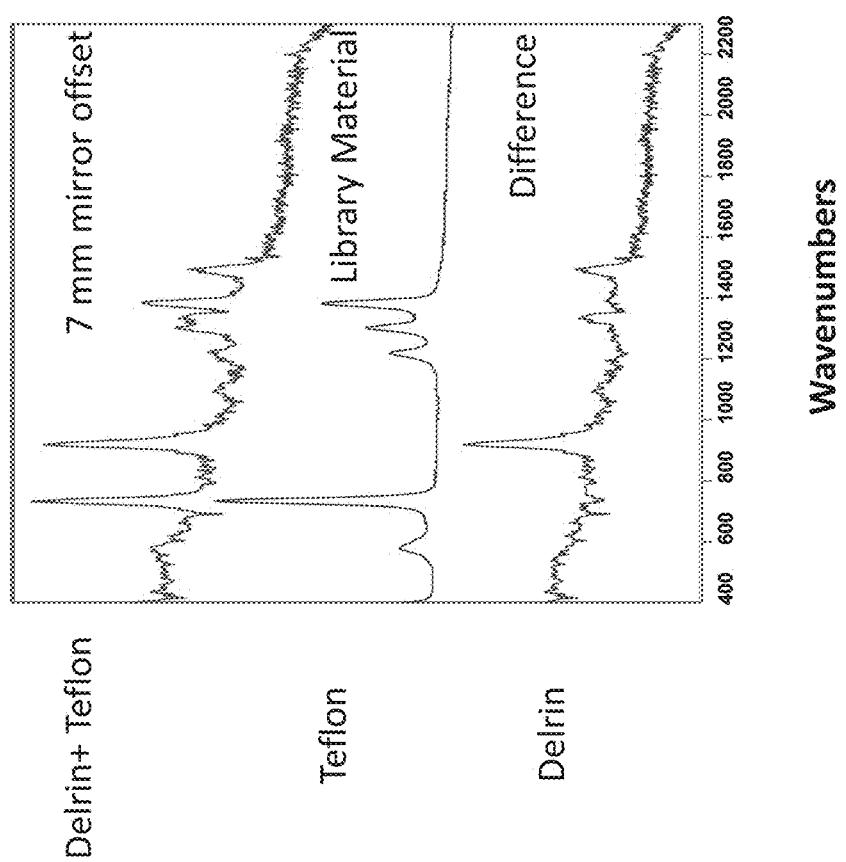
FIG. 8 depicts example of a spectral subtraction for a mixture matching approach for the system shown in FIG. 7.

An example of a spectral subtraction for a mixture matching approach for the system shown in FIG. 7 is illustrated in FIG. 8. This example method, for example, is also useful in the field of Raman spectroscopy for analysis of mixtures where the spectrum of a mixture is resolved in it individual components by library searching and subtraction. In FIG. 8, a sample taken with a 7 mm offset is shown as the top spectrum corresponding to "Delrin+Teflon." A representation of a spectrum for Teflon is stored in a library (e.g., in the device or accessible by the device). The library spectrum representation for Teflon may be subtracted from the combined spectrum (Delrin+Teflon) to obtain a difference spectral representation as shown in FIG. 8 as the resulting Delrin spectrum.

Figure 9:
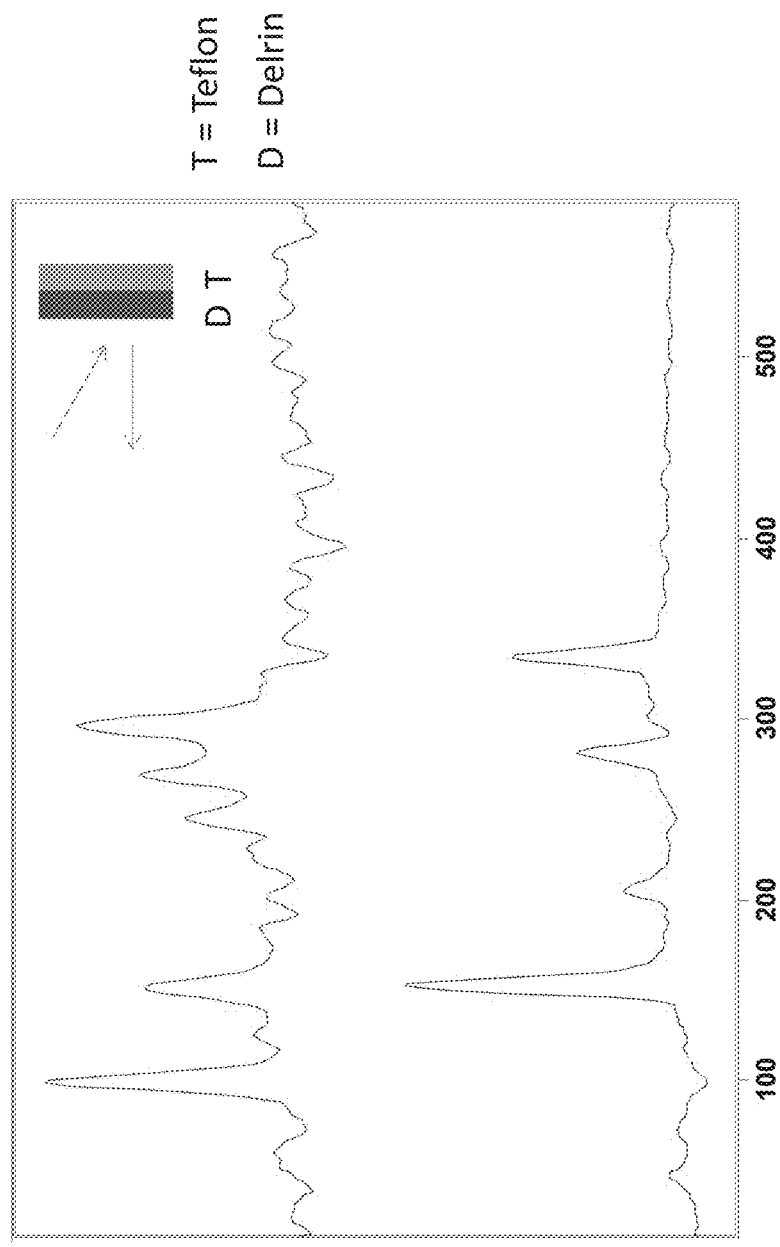
FIGS. 9, 10 and 11 depict example methods using multiple data points at different angles where a multispectral method of Principle Component Analysis or Independent Component Analysis was used to extract the signal from the two layers.
Figure 10:
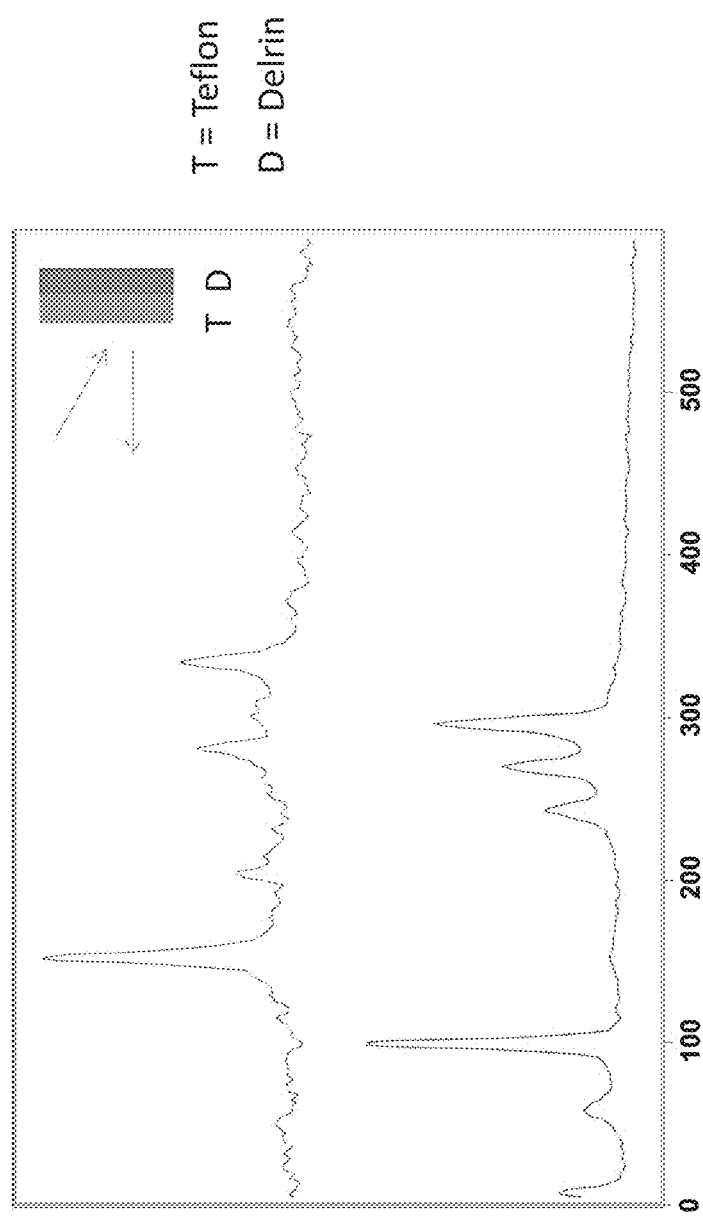
Figure 11:
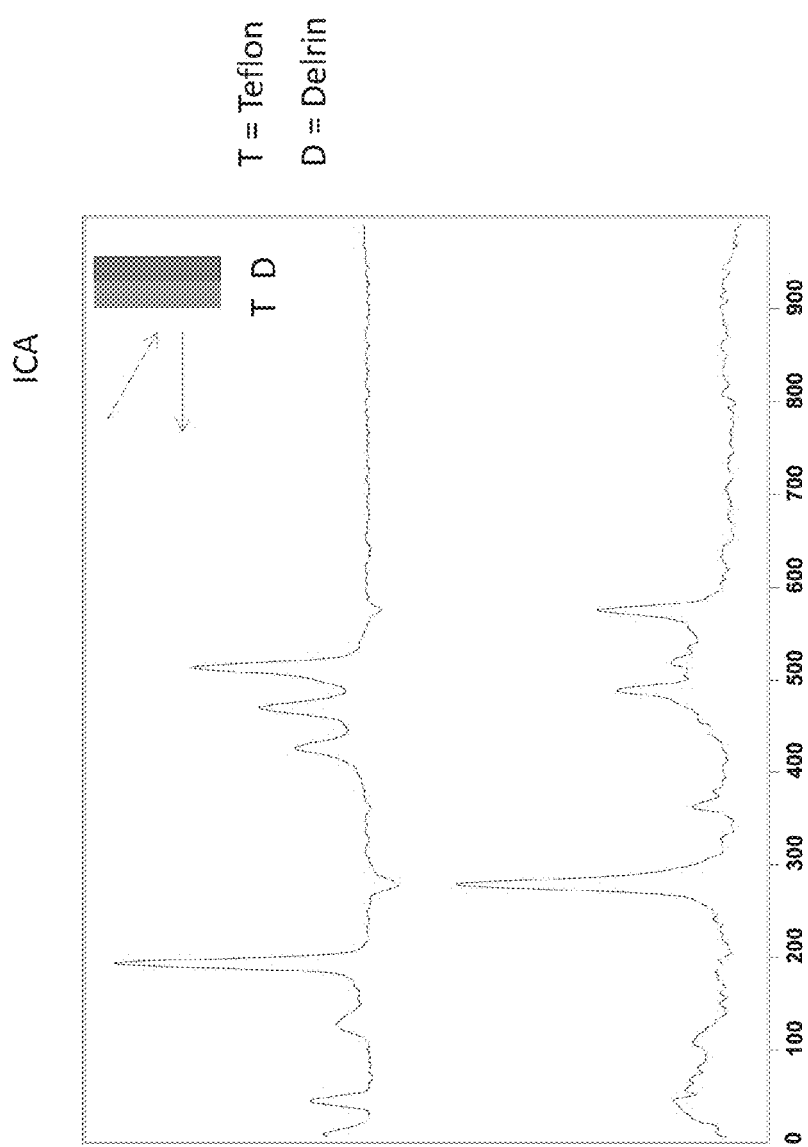

FIGS. 9, 10 and 11 illustrate the same method using multiple data points at different angles where a multispectral method of Principle Component Analysis or Independent Component Analysis was used to extract the signal from the two layers.

Figure 12:
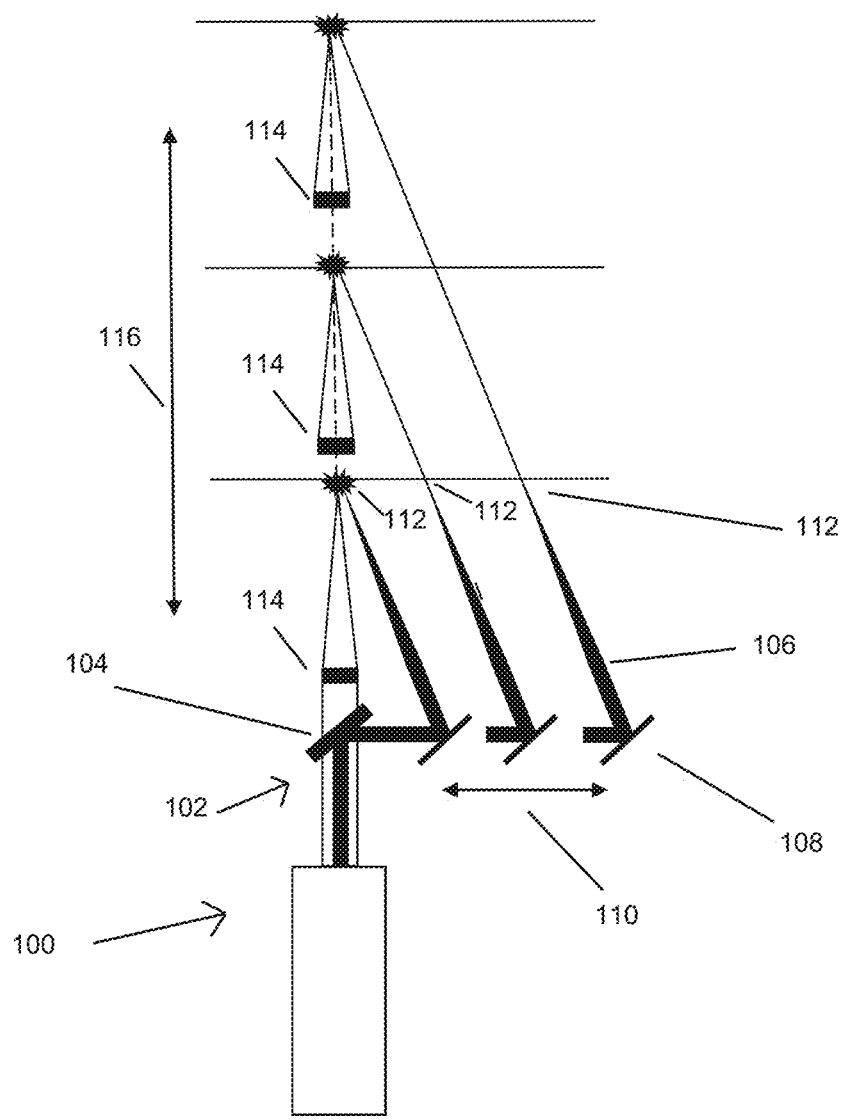
FIG. 12A depicts an example implementation of a spectrometer in which an optical system of the spectrometer is configured to direct an incident beam toward one or more moveable mirrors of the spectrometer.
FIG. 12B depicts an example implementation of a spectrometer in which an optical system of the spectrometer is configured to direct an incident beam toward one or more moveable mirrors of the spectrometer.
Figure 12B:
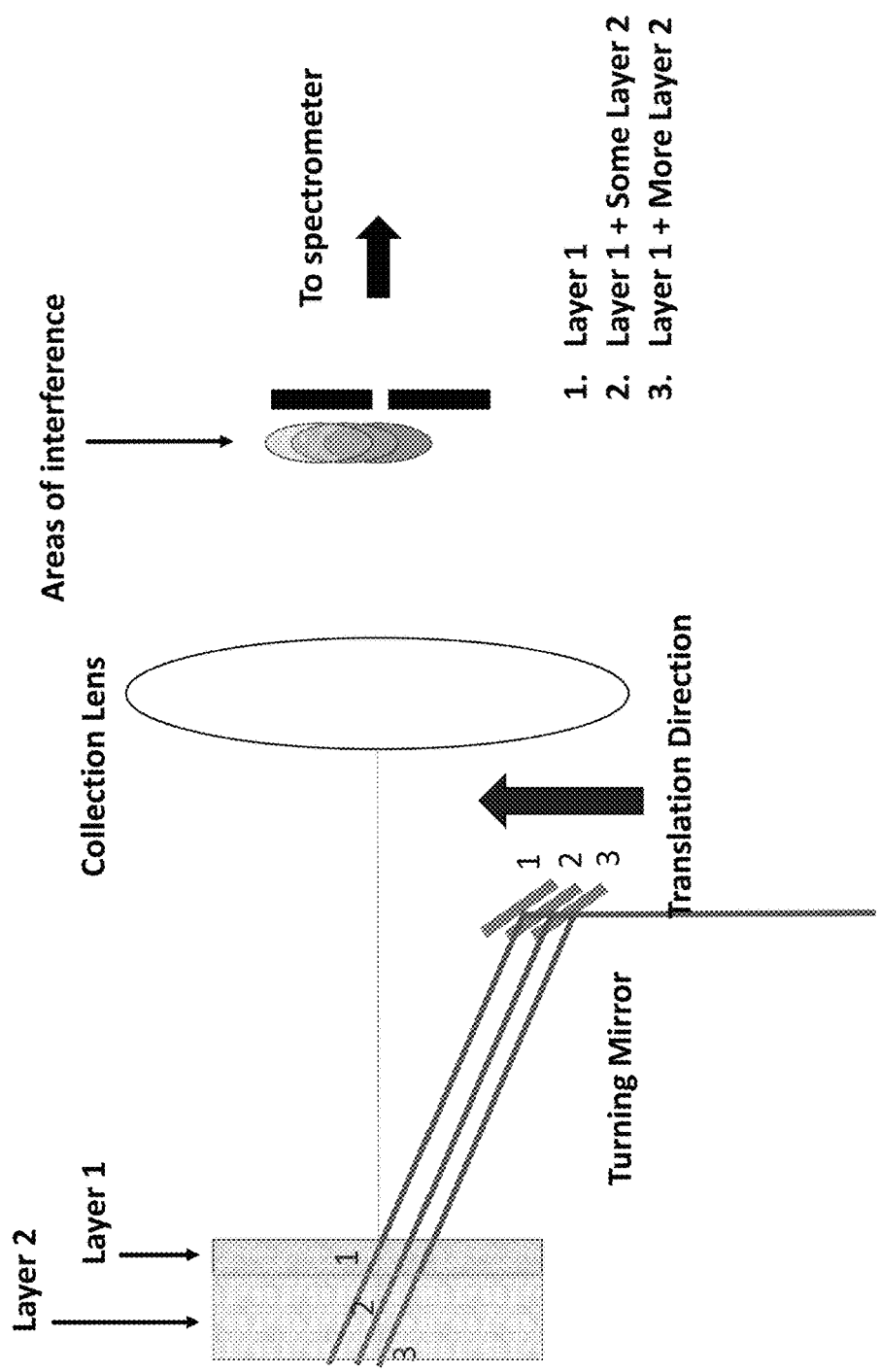

FIGS. 12A and 12B illustrate two example implementations of a spectrometer 100 in which an optical system 102 of the spectrometer 100 comprises a beam splitter 104 that directs an incident beam 106 toward one or more moveable mirrors 108. The one or more moveable mirrors 108, in turn, reflect the incident beam 106 toward a sample. In the implementation shown in FIG. 12A, for example, one or more moveable mirrors 108 are displaceable laterally along a translation axis 110 but are configured to reflect the incident beam at a common angle toward the sample from one or more displaced locations along the translation axis 110. In this particular implementation, by directing the incident beam 106 at a common angle toward the sample from different laterally displaced locations, the incident beam enters the sample (and/or a container or other material adjacent the sample) at laterally displaced locations 112 and reach a point in front of a collection lens at different depths of the sample/material. The incident beam is passed through a spatial filter to a spectrometer.

In the implementation shown in FIG. 12A, for example, a moveable lens 114 of the spectrometer 100 can also be moved along an axis 116 toward or away from the sample to collect a spectroscopy signal. In this implementation, the collection lens 114 may be moved closer to receive the spectroscopy signal from an illumination of the sample and/or material deeper within the sample and retracted to receive a signal from an illumination of the sample and/or material shallower within the sample or at an outer boundary of the sample. In other implementations, however, the collection lens may be fixed.

In the implementation shown in FIG. 12B, for example, the sample includes a multi-layer sample (e.g., a sample container wall and a sample disposed within the container) indicated in FIG. 12B as layers 1 and 2, although any number of layers and/or materials may be included. In this implementation, the mirror receives an excitation signal (e.g., directly from an excitation source such as a laser or via one or more optical elements such as a beam splitter shown in FIG. 12A) and reflects it toward the sample at a common angle from translated locations 1, 2, 3 along a translation axis as described above with reference to FIG. 12A. In this implementation, as the reflected excitation beam is translated, the resulting spectroscopy signal includes varying contributions from the different layers. The spectroscopy signal, in this example, may include varying contributions correspond to different depths 1, 2, 3 within the sample at a collection axis as the excitation beam disperses through the sample. A collection lens receives a spectroscopy signal from the sample along the collection axis and focuses the signal at a filter (e.g., the spatial filter shown). Depending on the position of the translating mirror, the signal at the filter and in turn the spectrometer correspond to varying layer(s) of the sample. In the particular example shown in FIG. 12B, for example, Layer 1 at position 1, Layer 1 plus a portion of the signal corresponding to Layer 2 at position 2, Layer 1 and a greater portion of the signal corresponding to Layer 2 at position 3, etc.

FIG. 13 shows another example implementation of a spectrometer in which the optical system of the spectrometer includes separate excitation and collection optical paths. In this particular example implementation, one or more mirrors (1,2,3) are positioned in an arrangement in which the mirrors reflect an incident beam at different angles from different lateral positions toward the sample. In this example, each of the incident beams from the different mirrors (1,2,3) are directed toward a common location on the sample and/or material (in this case the translucent material layer (e.g., a container) positioned adjacent the sample layer. Each of the incident beams pass through the same position (A) on the external surface being illuminated with the incident beam. As the beams pass through the layers, the directions of the individual incident beams intersect with an axis (B) of a collection optical path at varying distances from the collection optics of the spectrometer. In this manner, spectroscopy signals returned from the individual incident beams represent signals corresponding to different depths being sampled.

The mirrors (1,2,3) may represent individual fixed mirrors located at different lateral positions and configured at the different angles, or may include one or more moveable mirrors that are positioned at different lateral locations at different angles to reflect the incident beam to a common position (A).

Figure 14:
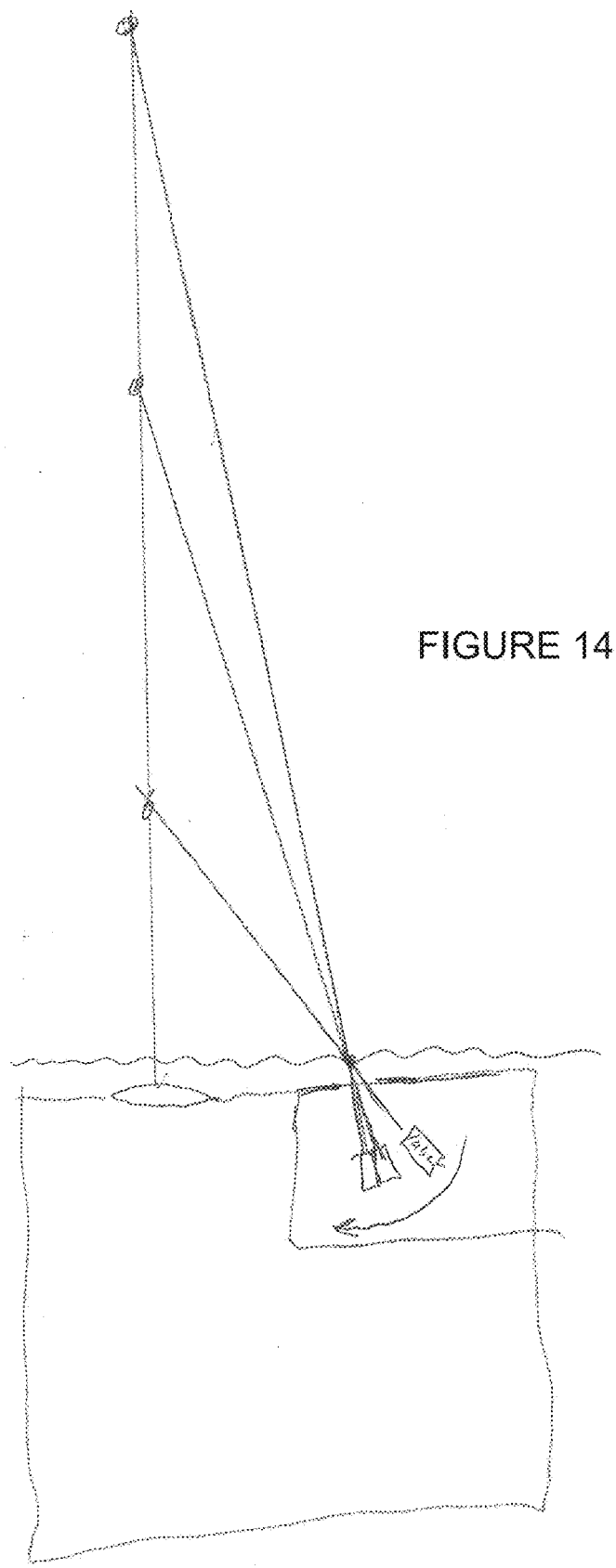
FIG. 14 depicts an example implementation of a spectrometer configured to direct an incident beam at varying angles through a common location at a surface of a sample and/or material.

FIG. 14 illustrates yet another example implementation of a spectrometer in which the optical system of the spectrometer includes a light source (e.g., a laser) or reflective optical element (e.g., a mirror) positioned such that the light source is moveable along an arc so that an incident beam is directed at varying angles through a common location at the surface of a sample and/or material adjacent to the sample similar to the incident beams described with reference to FIG. 13. Although FIG. 14 shows the light source being moveable, a light source may also direct an incident beam onto one or more reflective optical elements (e.g., mirrors) that can move in a similar manner to the light source shown in FIG. 14.

Figure 15:
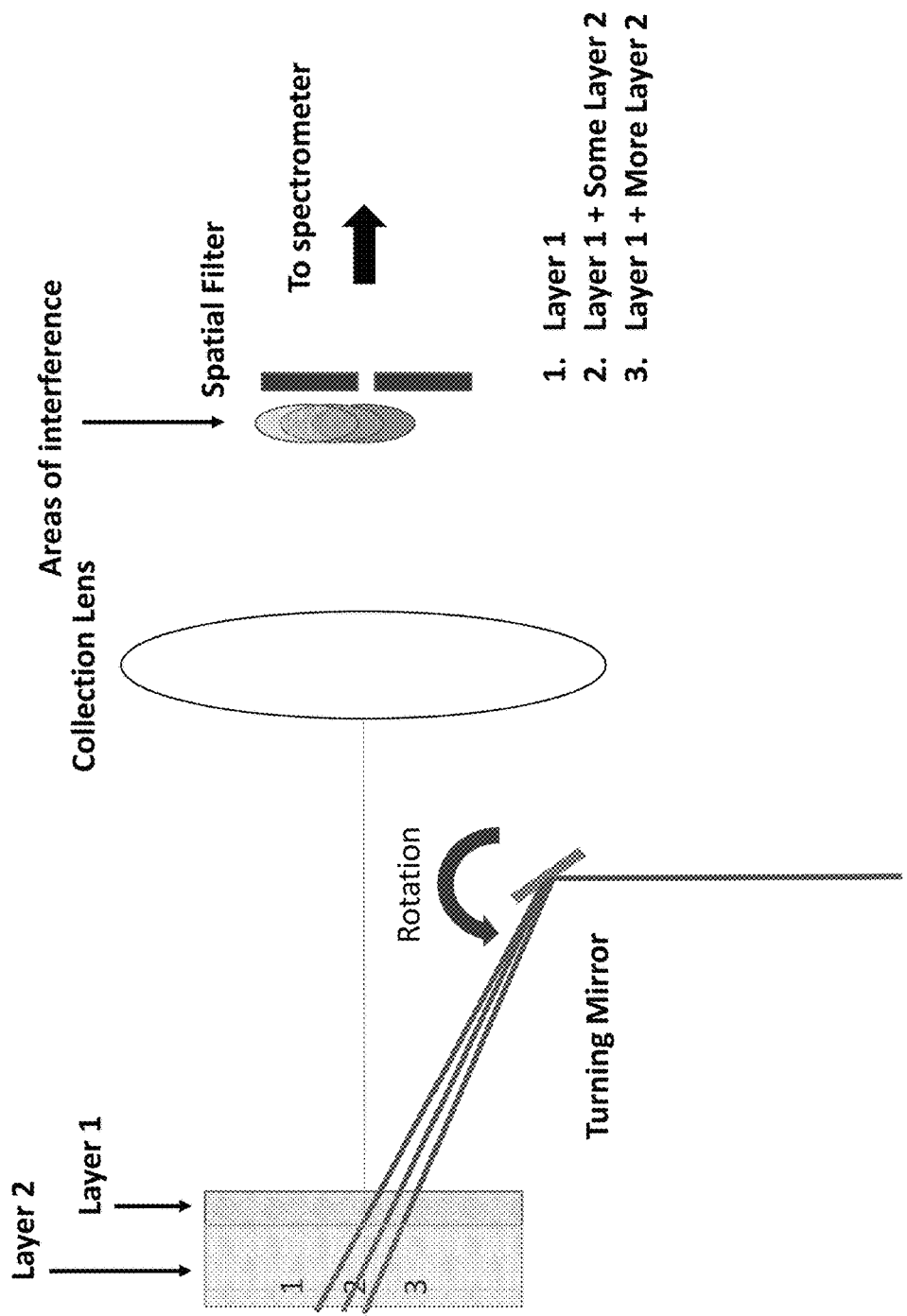
FIG. 15 depicts an example implementation of a spectrometer configured to direct an excitation beam toward the sample at different angles.

FIG. 15 shows another implementation of a spectrometer. In this implementation, a mirror is adapted to be rotated or turned to change an angle of an excitation beam (e.g., laser) directed toward a multi-layer sample. In the particular implementation shown in FIG. 15, the excitation beam is shown directed toward the sample at three different angles such that the beam disperse generally toward the second layer at points 1, 2, 3 beyond a collection axis, at a collection axis and before a collection axis. Although the collection angle is shown as being generally orthogonal to a surface of the first layer of the sample, the collection angle may be angled at another angle from the surface of the first layer of the sample. A collection lens collects the spectroscopy signal (e.g., a Raman spectroscopy signal) and focuses the spectroscopy signal on a spatial filter. The spatial filter removes at least a portion of an interference corresponding to the first layer as will be described in further detail with respect to FIG. 16. The spatially filtered spectroscopy signal is then directed by an optical system of the spectrometer to a detector of the spectrometer.

Figure 16:
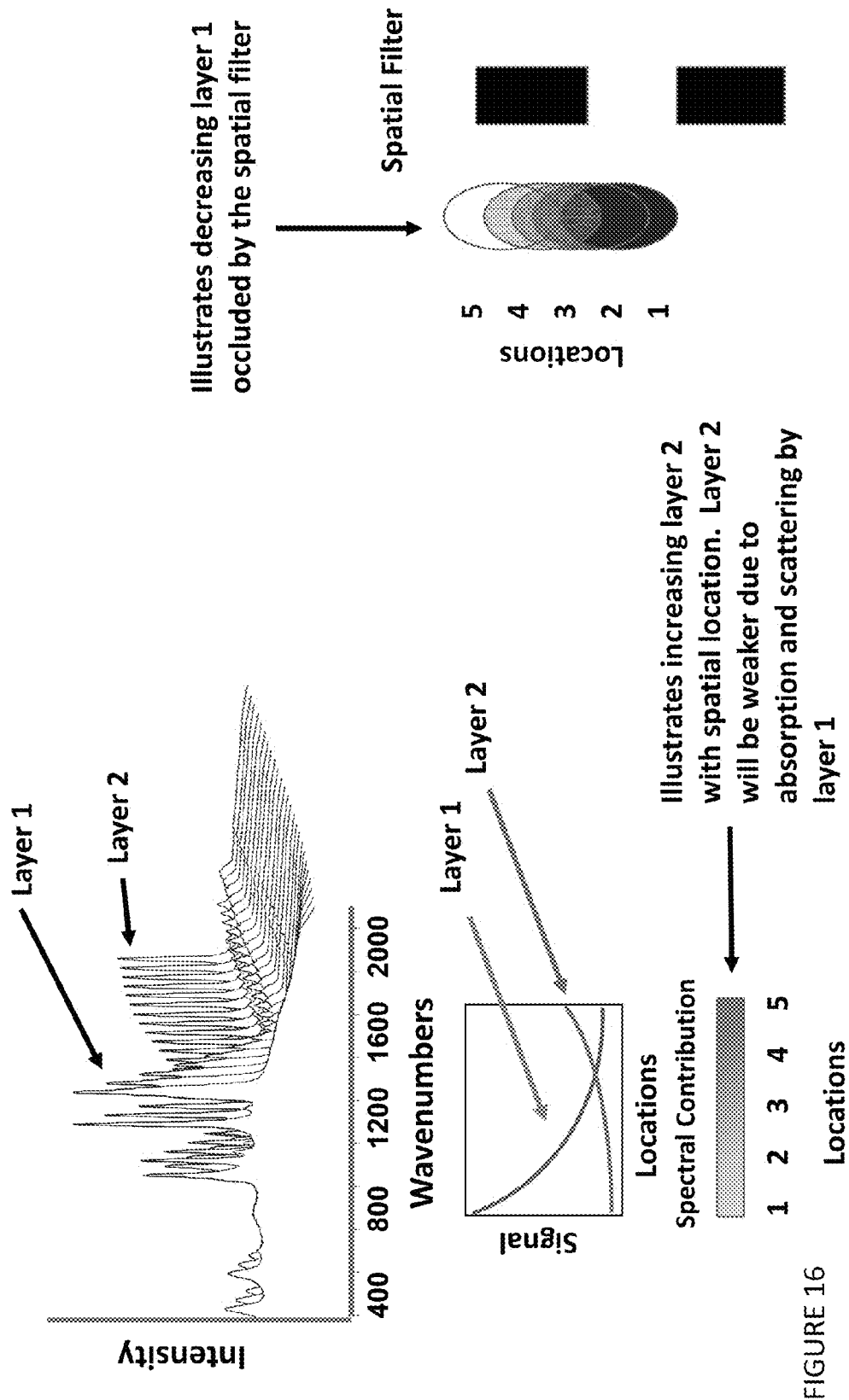
FIG. 16 depicts an example implementation of a method for determining one or more spectra corresponding to a second layer of a sample.

FIG. 16 shows an example graph of a method for determining one or more spectra corresponding to the second layer of the sample shown in FIG. 15. In this implementation, the structure of the data illustrated in FIG. 16 provides insight into methods of distinguishing different layers. Layer 1 represents an external (first layer) of the material and Layer 2 is a second layer disposed internally to layer 1. A spectra from Layer 1 decreases very rapidly, at a much faster rate, than the subsequent layers. If there is only one subsequent layer the signal of that layer is relatively consistent.

Figure 17:
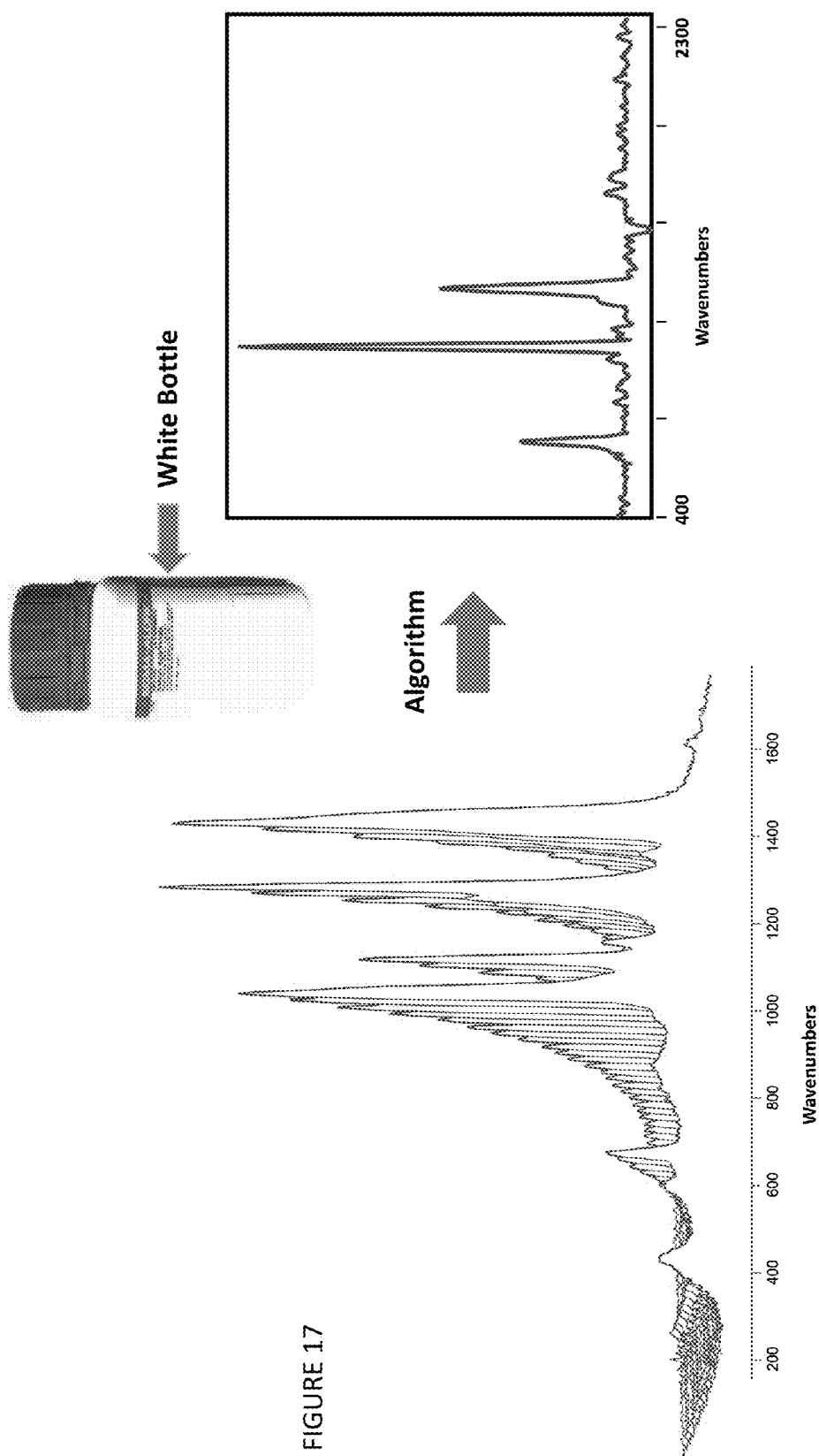
FIG. 17 depicts an example implementation of a method of using subtraction of a normalized standard deviation from an average to produce a spectrum of a second layer.

Mathematically different rates of decay can be used to separate components of the data set into the different components. For example, a Least Squares analysis of the data along each spectral point shows that the second layer is mostly contained in the first component of the Least Squares polynomial and the rapidly decaying spectral information is contained in the second component. Likewise, statistically the average of the data along the spectral data points is largely composed of the second layer and the standard deviation of the along the spectral data points represents the variance in the data and largely is composed of the first layer of the sample. A subtraction of the normalized standard deviation from the average produces a pure spectrum of the second layer. This method is illustrated in FIGS. 17 and 18.

Figure 19:
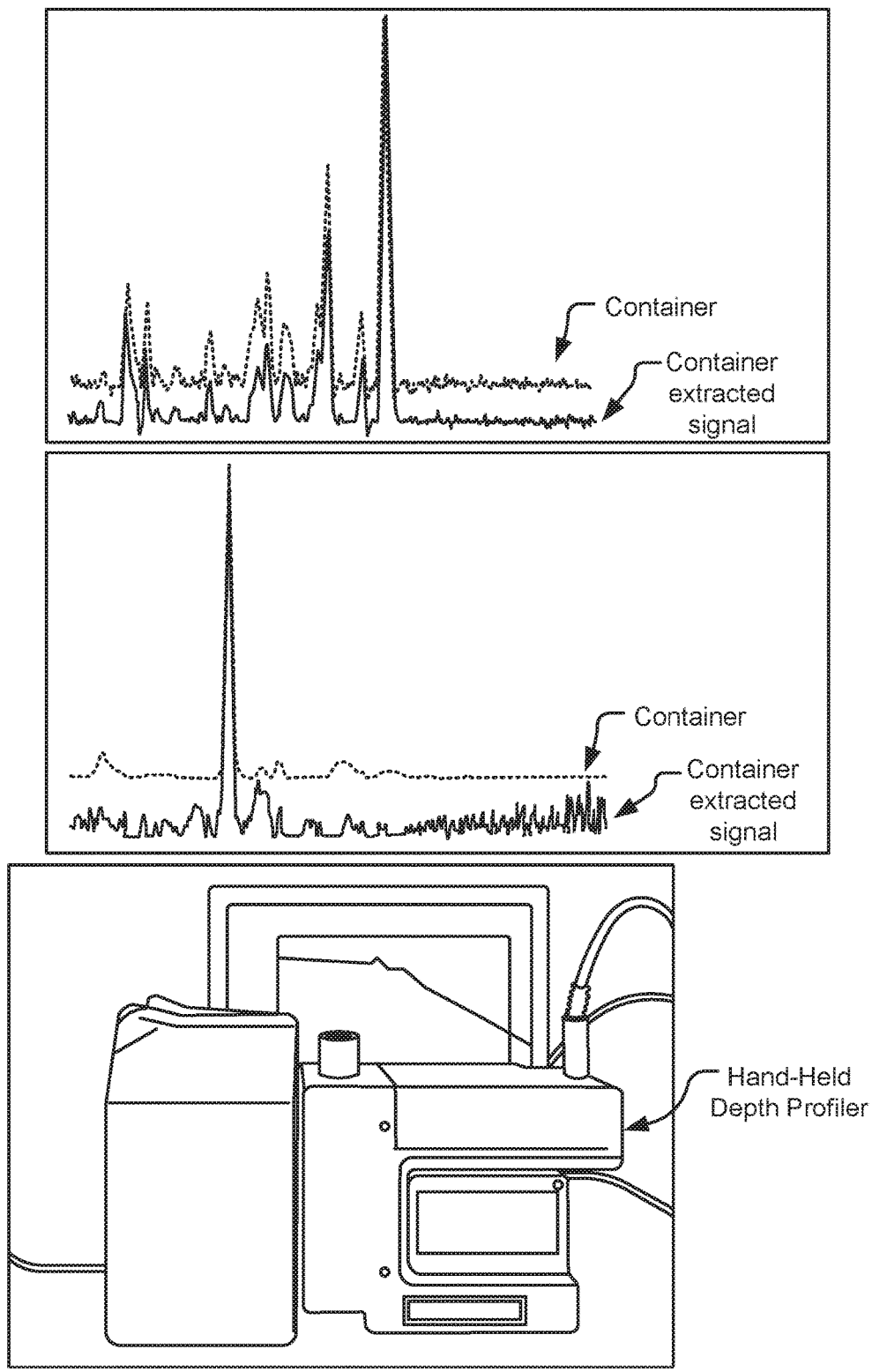
FIG. 19 depicts an example implementation of a method of extracting spectra for an external container layer and an internal content layer disposed within the external container layer.
Figure 19:
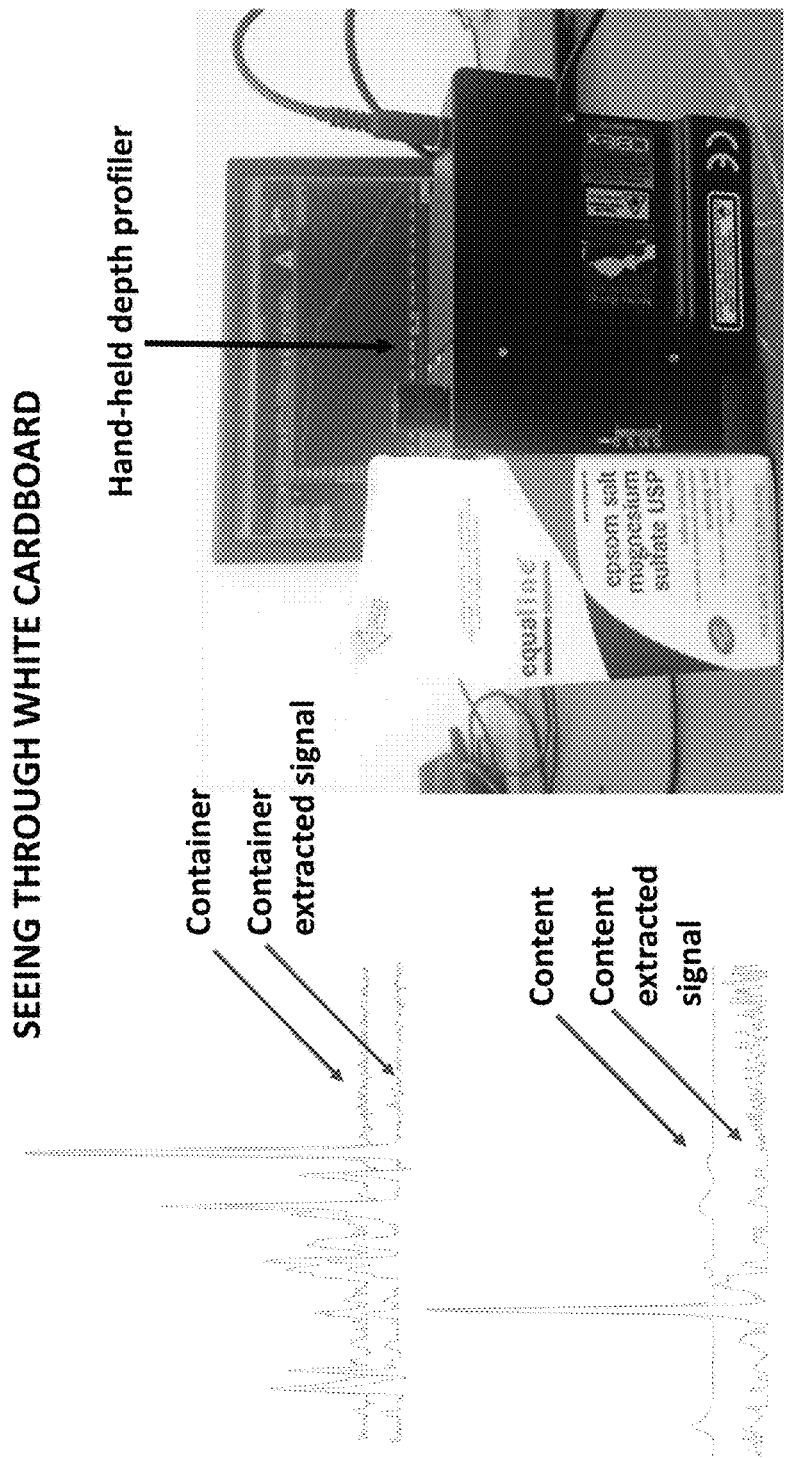

FIG. 19 shows another example of extracting spectra for an external container layer and an internal content layer disposed within the external container layer. In this particular implementation, the container comprises a white cardboard layer. Spectra of the container and contents of a carton of Epsom salts (Magnesium Sulfate) are shown in FIG. 19. In this example, spectra were collected at multiple angles. A least squares analysis of the spectra was carried out at each wavenumber element. A comparison of the extracted signal from the least squares algorithm and contents are illustrated. As shown in FIG. 16, the intensity of spectral features of the container decrease in a nonlinear relationship with respect to the off-axis angle. When a quadratic equation is formed with the least squares analysis, the equation $a+bx+cx^2$ relates more container content in the b value than in the a value. Subtraction of the a normalized b value from a leads to separation of the content spectrum from the container spectrum.

Figure 20:
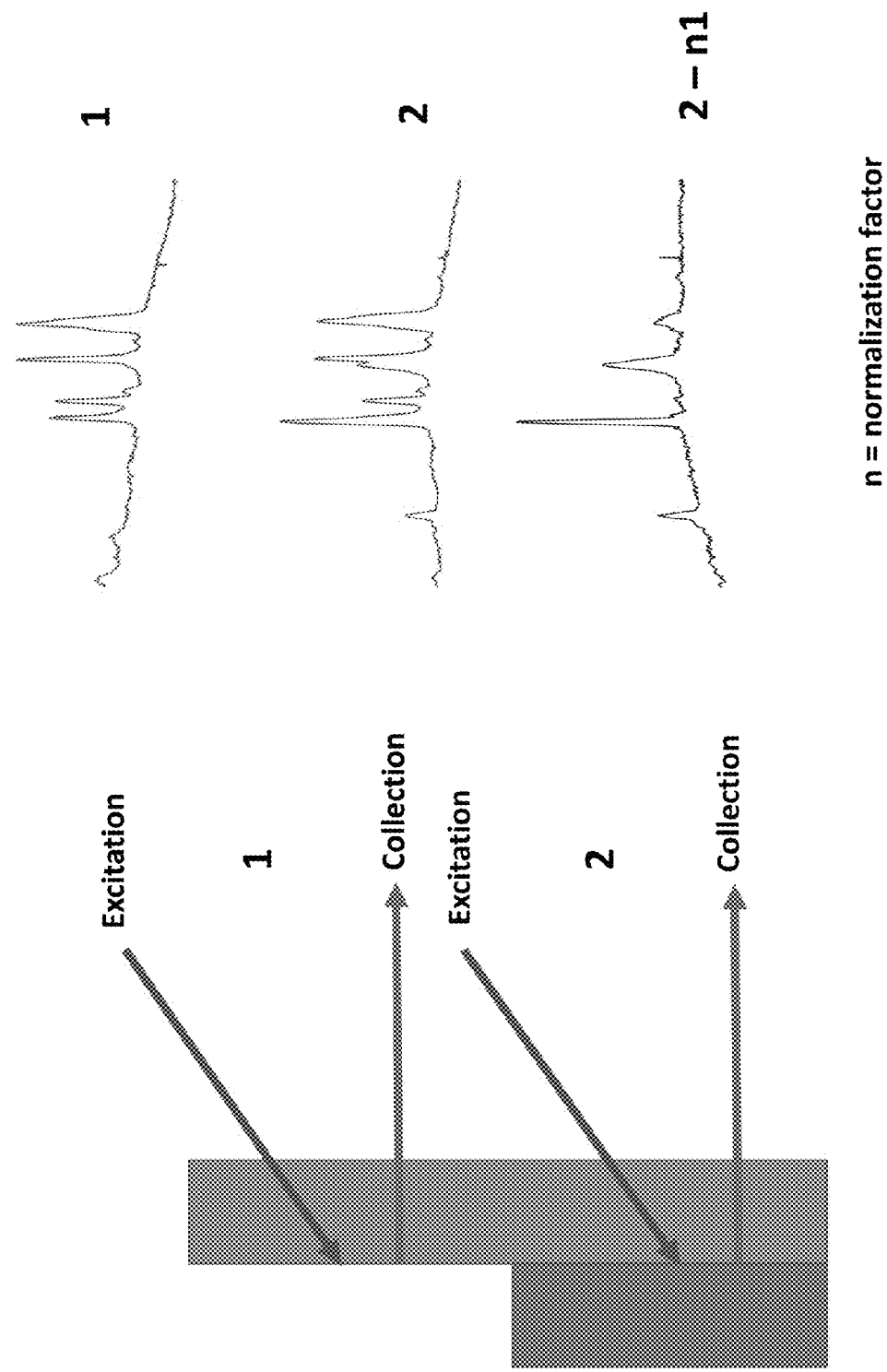
FIG. 20 depicts an example implementation of a system configured to sample a material disposed within/behind an outer layer.
Figure 21:
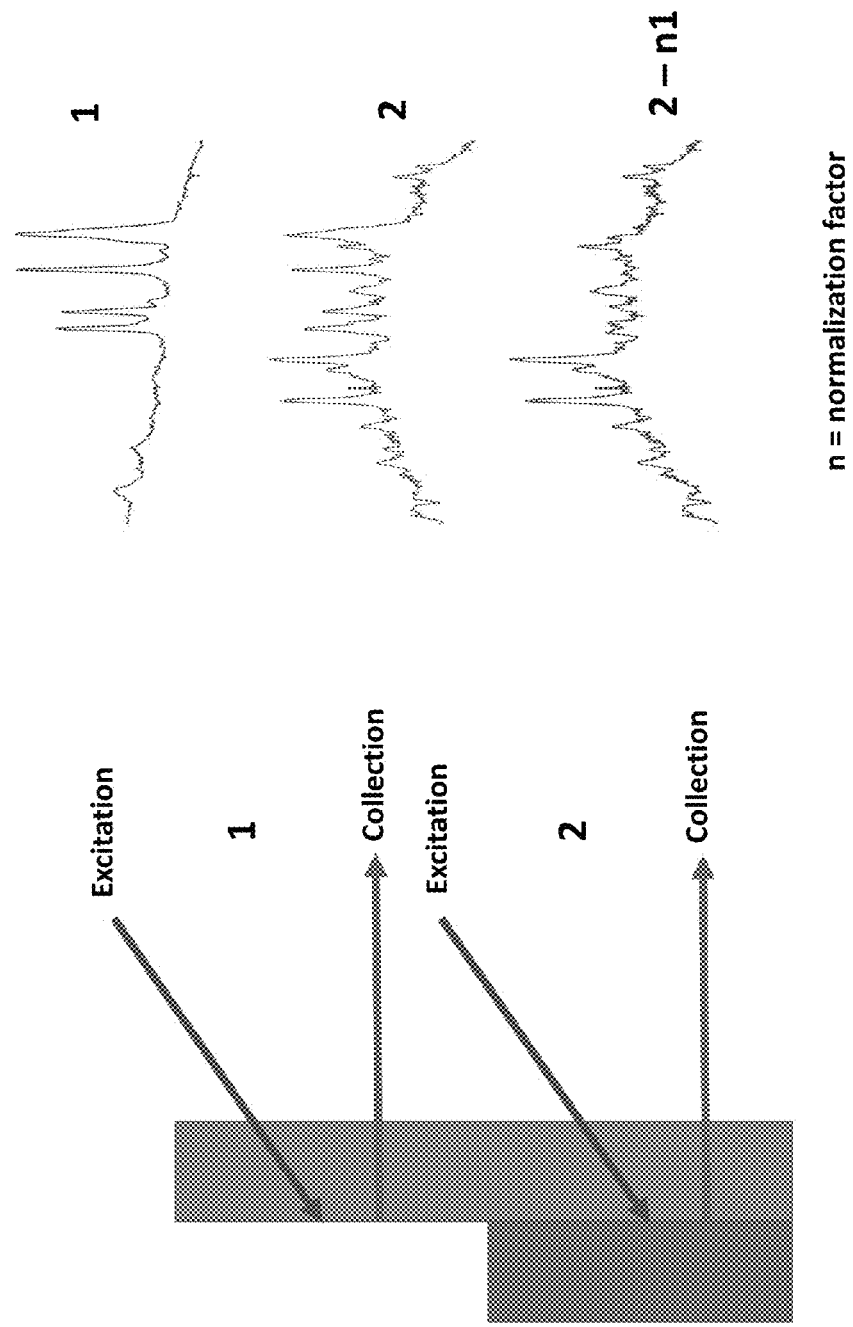
FIG. 21 depicts another example implementation of a system configured to sample a material disposed within/behind an outer layer.

FIGS. 20 and 21 show other implementations of systems for sampling a material disposed within/behind an outer layer. The material, for example, may comprise a material disposed within a container (e.g., within a plastic or paper container). In this implementation, an excitation beam is first directed into the external layer at a first location (1) where the internal material is not disposed adjacent to/behind the external layer. In this implementation, the spectroscopy signal is collected along a first collection axis and a spectrum corresponding to the first outer layer is determined. An excitation beam is then directed at an angle through the external layer at a second location (2) and into a second layer that is disposed adjacent to/behind the first layer at the second location. Although FIGS. 20 and 21 show example in which a first location is sampled first, the order of sampling the first and second layers may be reversed or performed simultaneously in various implementations.

As discussed further herein, the second spectra collected from the second location corresponding to a combination of the first and second layers can be normalized (e.g., by a normalization factor n) and the normalized second spectrum may be subtracted from the first spectrum (2−n1).

The spectra shown in the example of FIG. 20 correspond to contents in a container including a relatively strong Raman scattering material (bicarbonate), and the spectra in the example of FIG. 21 correspond to contents in a container including a relatively weak Raman scattering material (citric acid). As can be seen in the Figures, the method was successful in both examples.

Figure 22:
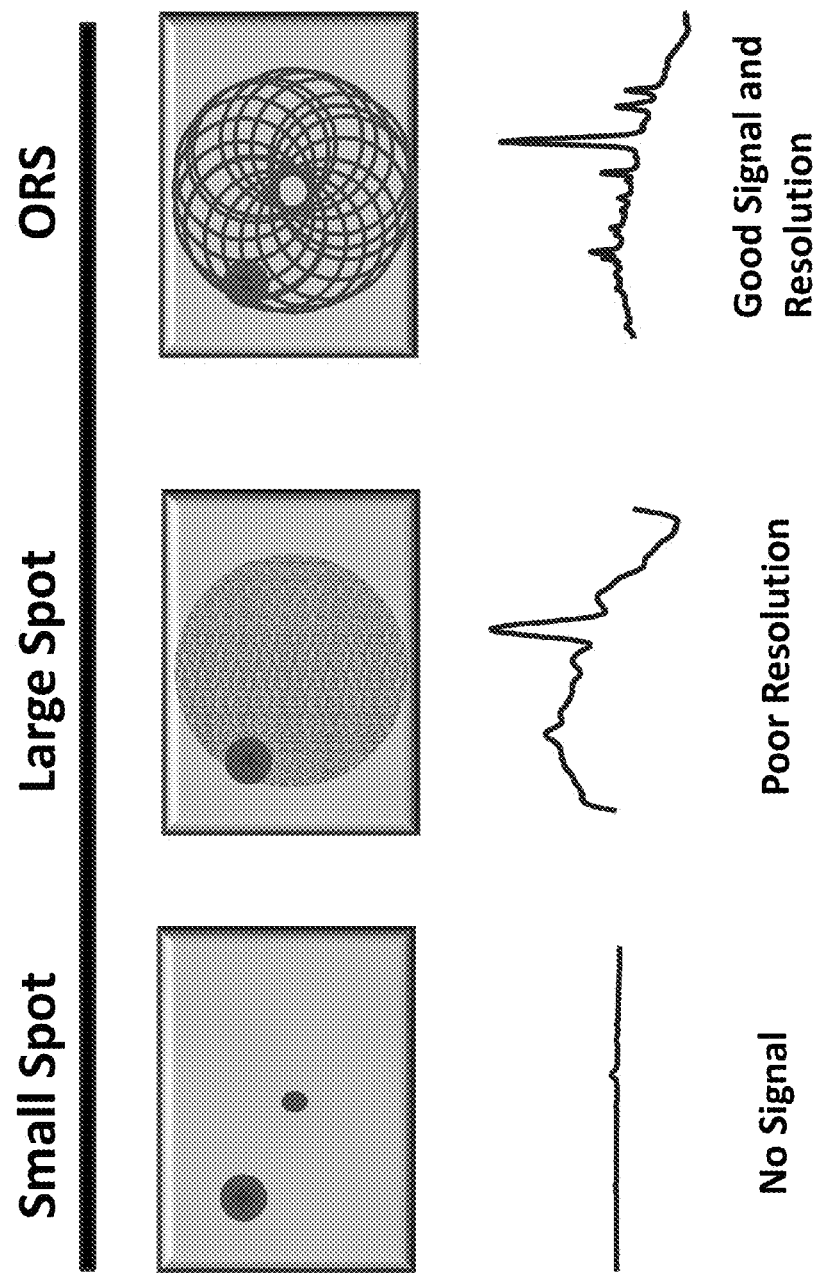
FIG. 22 depicts three example implementations of spectroscopically sampling a surface with an incident spectroscopy beam, such as a laser beam of a Raman spectrometer.

FIG. 22 shows three examples of spectroscopically sampling a surface with an incident spectroscopy beam, such as a laser beam of a Raman spectrometer. In the first example, a single focused beam illuminates a spot on the surface. While the focused beam allows for a relatively high resolution sample of the spot illuminated by the focused beam on the surface, where the surface is not homogeneous, the illuminated spot may miss a particle or region of interest where the single illuminated spot does not illuminate the particle or region of interest on the sample surface. In this example, the particle or region of interest is not illuminated by the focused excitation beam and, thus, the spectrometer does not detect one or more particles in the identified region of interest that falls outside the focused beam.

In a second example, a larger excitation beam (e.g., a laser beam of a Raman spectrometer) illuminates a relatively larger region of the surface of the sample than in the first example. In this second example, the excitation beam is not as relatively tightly focused as the excitation beam in the first example and the spectrometer has a lower resolution than the spectrometer in the first example with the focused excitation beam. Thus, the spectrometer may have an insufficient resolution to detect one or more particles of interest in a region of the sample surface even where the excitation beam overlaps all or a portion of the region including the one or more particle of interest.

In the third example, a focused excitation beam is moved across the surface of the sample. The focused excitation beam may be moved (e.g., scanned, rotated or otherwise moved) in a pattern and/or randomly across the surface of the sample, including the region of interest that includes the one or more particles to be detected. The focused excitation beam, in this third example, is likely to intersect the region of interest and maintains a relatively high resolution as the excitation beam is moved across the surface of the sample. Thus, the spectrometer is able to detect the one or more particles of interest in the region. Examples of devices that are adapted to move an excitation beam across the surface of the sample, such as shown in the third example of FIG. 15, are described in U.S. Pat. No. 8,867,033 and patent application Ser. No. 13/161,485 filed on Jun. 15, 2011, Ser. No. 12/268,419 filed Nov. 10, 2008 and Ser. No. 13/907,812 filed May 31, 2013, each of which is hereby incorporated by reference in their entirety for all they teach and suggest.

Figure 23:
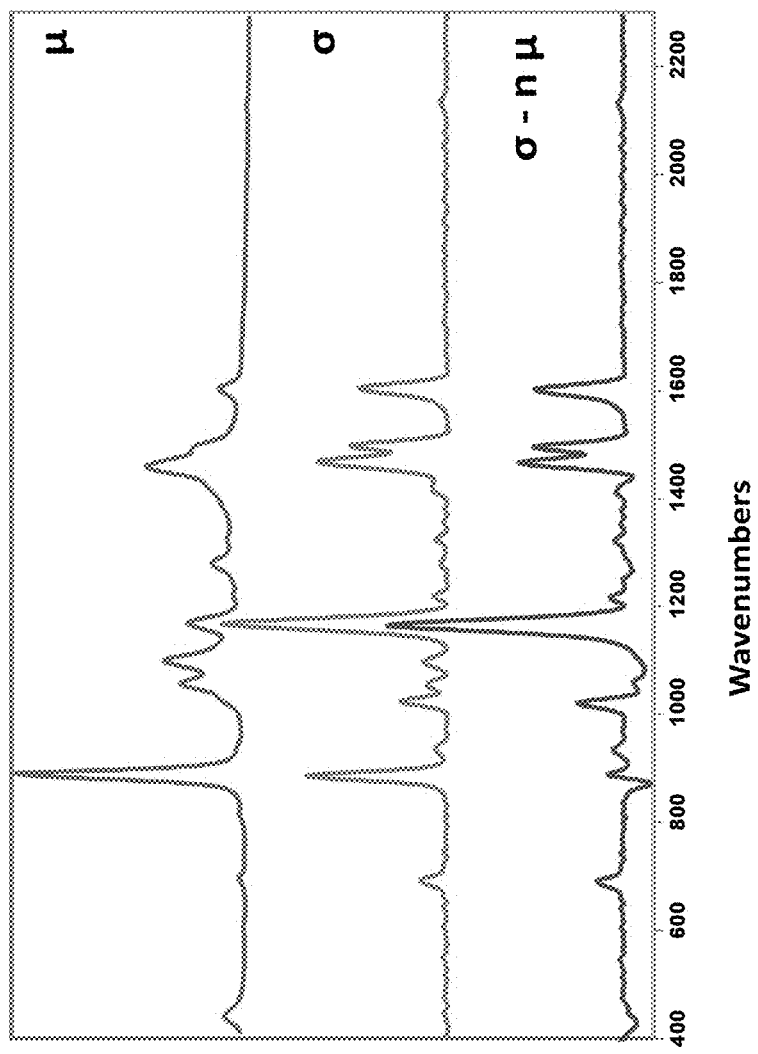
FIG. 23 depicts an example implementation of a statistical method to isolate signals of trace discrete materials from an overwhelming matrix background.

FIG. 23 shows an example graph that can be used to illustrate an example of a statistical method to isolate signals of trace discrete materials from an overwhelming matrix background. In the relatively large excitation beam of the second example shown in FIG. 22, for example, a small signal corresponding to the target particle(s) of interest that is present in a spectrum taken from the entire region of the sample illuminated by the relatively large excitation beam that primarily corresponds to the material of the sample surrounding target particle(s) of interest. Where the resolution of the spectrometer due to the size of the beam is too low to distinguish the spectral features of the particle(s) of interest from the remainder of the sample, the particle(s) are likely to not be detected.

Where multiple, discrete spectra are collected during the movement of a focused excitation beam across a surface of the sample as shown in the third example of FIG. 22, an array of spectra data may be generated. A majority of the array will correspond to the material (matrix) of the sample and a minority of the array data will include primarily the target(s) and secondarily the material (matrix) of the sample. In this implementation, the target spectrum can be separated from the majority signal of the matrix sample material. Since the majority of the spectra originate from the matrix sample material, the spectra are typically very similar. A standard deviation of the signal at each wavenumber element will be small. On the other hand, the target spectrum/spectra may be present in a minority (e.g., one or more) of the spectra of the array and those signals will deviate strongly from the average matrix sample material signals.

In the example shown in FIG. 23, for example, a sample of a small 100 nm gold nanoparticle with a trace of a target material/particle(s) was used with an ethanol for the sample material. In this example, algorithm and data from a DRS analysis of particles floating in a solution are shown. A normalized average (mean) spectrum ($\mu$) contains mostly the predominant solution or surface material. A standard deviation spectrum ($\sigma$) contains a large amount of the weaker particles in the solution or on the surface. If the mean spectrum is normalized to its equivalent intensities in the standard deviation spectrum and subtracted from the standard deviation the resultant spectrum is the of the particles. Thus, the difference between a standard deviation spectrum ($\sigma$) and a normalized average spectrum ($\mu$) produce a pure spectrum of the target material. In this example, the resultant target spectrum can be achieved autonomously without the need of an operator to search for the target as would be required with a Raman (or other spectroscopic) microscope and may thus be achieved with a relatively lightweight and portable Raman (or other spectroscopic) system.

Figure 24:
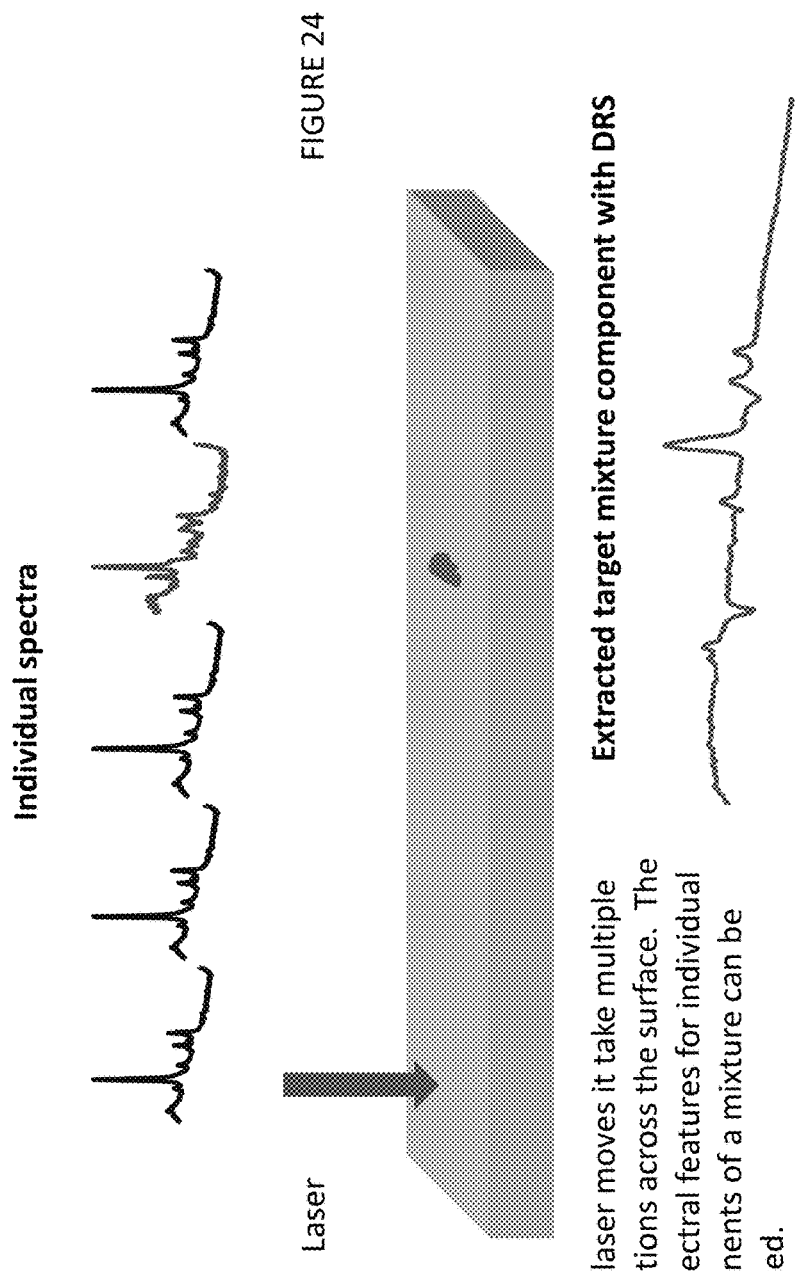
FIG. 24 depicts an example implementation of a dynamic scattering system including spatial separation.

FIG. 24 shows an example of a dynamic scattering system (e.g., a dynamic Raman scattering system) including spatial separation. In this example an excitation beam (e.g., a laser) moves across a surface of a sample (e.g., using a stepper motor) and a spectrometer takes multiple acquisitions across the surface. The multiple acquisitions provide multiple unit spectral features for individual components that may be distributed or otherwise disposed on the surface of the sample. An extracted spectrum of a target can be determined, such as using a statistical approach as described above with reference to FIG. 23, a principle component analysis or other statistical or mathematical approach.

Further each individual spectrum taken in the example shown in FIG. 24 may be collected during the movement of a focused excitation beam across a surface of the sample as shown in the third example of FIG. 22. Thus, an array of spectra data may be generated for each individual sample shown in the example of FIG. 24.

Figure 25:
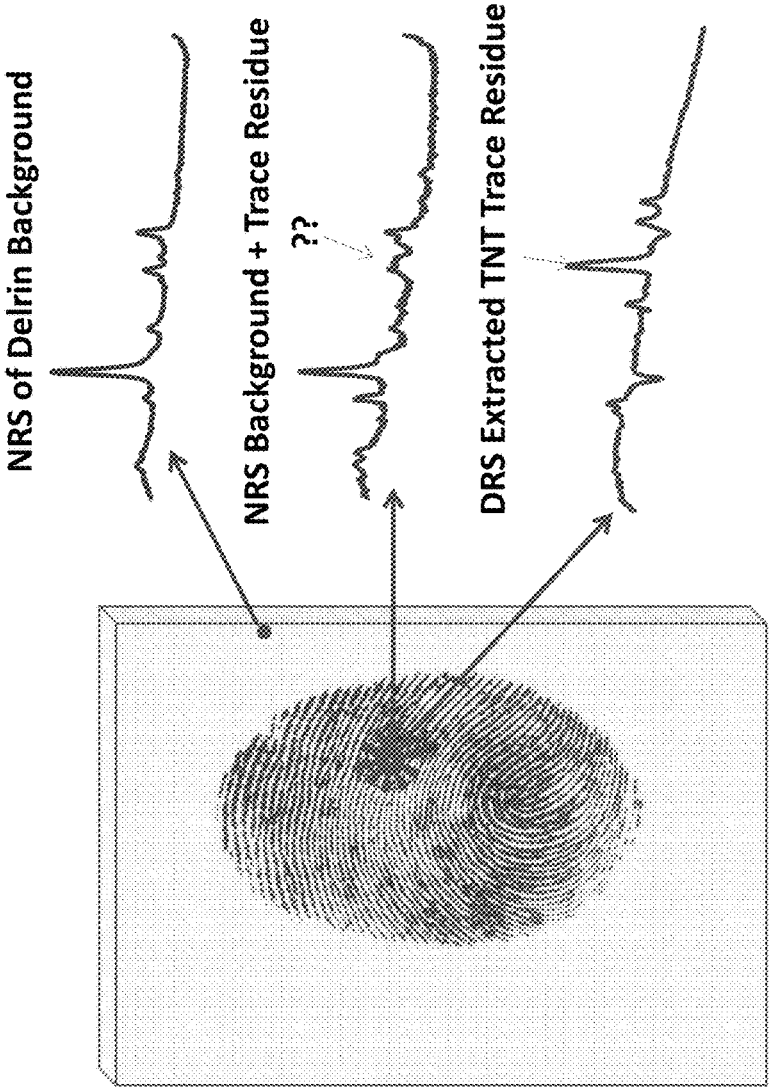
FIG. 25 depicts an example implementation of a method for which in a trace residue present on a fingerprint imprinted on a background material may be detected.

FIG. 25 shows another example, in which a residue present on a fingerprint imprinted on a plastic (e.g., Delrin) background material may be detected. In this example, a residue (e.g., a trace residue) can be detected by separating the spectral features of the background (e.g., Delrin) from the target residue (e.g., trace residue), such as described above with respect to FIGS. 23 and 24.

FIG. 26 shows another example implementation of a spectroscopic system in which an excitation beam is fixed at an angle to a surface of a multi-layered sample (e.g., Layer 1 and Layer 2). The first layer, for example, may be sampled such as shown in FIGS. 24 and 25. The second layer (and/or any additional layers) may be further sampled by changing the excitation angle and then moving (e.g., rotating, angling or otherwise moving) a mirror to move the excitation beam relative to the second layer (and/or any additional layers). The excitation angle may then be changed again, and then moved relative to the second layer (and/or any additional layers) using the mirror (or another mirror) any number of additional times.

Appendix B of U.S. provisional application 62/192,023 entitled Spectrometer and filed Jul. 13, 2015, which is incorporated by reference in its entirety as if fully set forth herein, provides additional example, implementations and methods related to spectrometers utilizing an off-axis excitation.

In yet another alternative method to identify a material inside a container (or through a barrier), a library of popular container/barrier materials is used. In this particular implementation, for example, the method has an advantage by permitting the ingredients to be determined with a single acquisition. In one implementation, the method may be associated with longer integration times to maximize the signal to noise (sensitivity) ratio of a measurement. The implementation may also permit a very high quality with maximized signal to noise to be used as the subtrahend in the analysis and again this may produce an improved or optimal spectrum of ingredients.

Figures 28A, 28B, 28C:
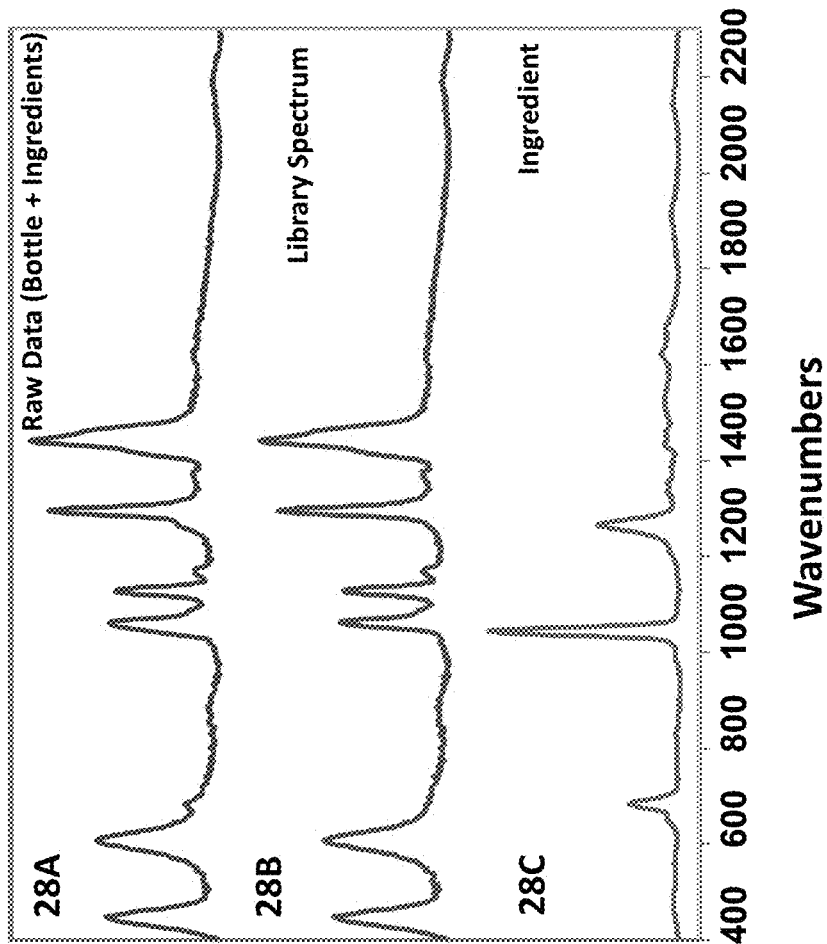
FIG. 28A depicts an example of a signal that contains both a container's spectrum and an ingredient's spectrum.
FIG. 28B depicts an example of a spectrum of a container material that may be stored in a library.
FIG. 28C depicts an example of a spectrum of a material within a container determined from the combined spectrum shown in FIG. 28A and the library spectrum shown in FIG. 28C.

An example implementation utilizing this concept of measurement is illustrated in FIG. 27. In this particular implementation, a single measurement is made with a laser excitation that is at an angle, Θ, between 90 and 180 degrees. The laser can also be adjusted to enter the container at a point which is not within the cone of collected light accepted by the spectrometer. This may produce a signal that contains both the container's spectrum and the ingredient's spectrum. This spectrum is illustrated in FIG. 28A. When a spectral library is searched that contains a spectra of container materials the top hit may correspond to the spectra of the container in some implementations. In this implementation, this true even though a small amount of ingredient spectra is contained within the spectrum in FIG. 28A. A Pearson correlation may be used to maximize the correlation between spectra which contain the largest amount of a common signal. In one example, a container material may be found even when a minor signal from an ingredient is present.

In this particular implementation, a library may contain a pure spectrum of the container material. In this example, this is illustrated in FIG. 28B. While not instantly apparent the spectrum in FIG. 28A differs slightly from that in 28B. Peak shoulders and small new peaks are present in FIG. 28A that are not in FIG. 28B. A Pearson determination ($r^2$) between the two, in this example, is 0.98. If the spectrum from FIG. 28B is subtracted from the spectrum in FIG. 28A the resultant is the ingredient. In this example it matches to sodium bicarbonate which is the ingredient. The sodium bicarbonate spectrum in FIG. 28C has a high signal to noise level for two reasons: the acquisition time was maximized ion this example since only one spectrum was required; and the library container spectrum has a high signal to noise entry acquired previously under not critical time constraints.

In one implementation, for example, this method could also use common mixture analysis methods for Raman spectroscopy. One such method is that described above. It also could be methods used on more advanced methods such as Principal Component Analysis or other methods.

Individual example implementations shown and described with respect to one or more Figures in this application introduce individual concepts that may be used in different implementations as well. Thus, discrete implementations described herein are not exclusive and different concepts described with respect to one or more implementations shown in one or more Figures are done so merely to simplify the description of individual concepts. Thus, one or more features introduced in one example may also be used in other examples that may be described with reference to different figures or implementations herein. For example, the concept of collecting a spectra during the movement of a focused excitation beam across a surface of the sample as shown in the third example of FIG. 22 to collect an array of spectra data may be used in combination with any of the implementations in which a spectrometer is configured to deliver an off-axis excitation incident beam to a sample. Similarly, different methods of collecting a spectroscopy signal may be used in combination with different methods of directing a off-axis excitation incident beam to a sample.

Although implementations of this invention have been described above with a certain degree of particularity, those skilled in the art could make numerous alterations to the disclosed implementations without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A spectrometer comprising:
   a light source adapted to provide an excitation incident beam;
   a detector adapted to detect a spectroscopy signal; and
   an optical system adapted to direct the excitation incident beam toward an entry region of a sample including first and second layers at a non-zero angle from a zero-angle collection reference, receive a spectroscopy signal from the sample and provide the spectroscopy signal to the detector, wherein the entry region is offset from a collection region of the sample,
   wherein the detector is adapted to remove a spectral interference component of the spectroscopy signal corresponding to at least one of the first and second layers.

2. The spectrometer of claim 1 wherein the detector is adapted to remove the spectral interference component through spectral subtraction.

3. The spectrometer of claim 1 wherein the detector is adapted to remove the spectral interference component through spectral subtraction of at least one known component.

4. The spectrometer of claim 1 wherein the detector is adapted to remove the spectral interference component through spectral subtraction of at least one known component stored in a library.

5. The spectrometer of claim 4 wherein the library stores spectral interference components of a plurality of known materials.

6. The spectrometer of claim 4 wherein the plurality of known materials includes a plurality of containers.

7. The spectrometer of claim 4 wherein the plurality of known materials includes a plurality of plastic containers.

8. The spectrometer of claim 1 wherein the detector is adapted to receive a plurality of spectroscopy signals from the sample.

9. The spectrometer of claim 8 wherein the plurality of spectroscopy signals correspond to a plurality of incident beams directed toward the sample at different angles and/or offsets from a zero-axis line, such as but not limited to the axis B shown in FIG. 13.

10. A spectrometer comprising:
    a light source adapted to provide an excitation incident beam;
    a detector adapted to detect a spectroscopy signal; and
    an optical system adapted to direct the excitation incident beam toward an entry region of a sample including first and second layers at a non-zero angle from a zero-axis collection reference, receive a spectroscopy signal from the sample and provide the spectroscopy signal to the detector, wherein the entry region is offset from a collection region of the sample,
    wherein the detector is adapted to compare a plurality of spectroscopy signals corresponding to a plurality of incident beams directed toward the sample from a plurality of different non-zero angles and/or offsets from the zero-axis collection reference to identify at least one component of the spectroscopy signal corresponding to at least one of the first and second layers of the sample.

11. The spectrometer of claim 10 wherein the optical system is adapted to receive the spectroscopy signal at least generally along the zero-axis reference.

12. The spectrometer of claim 10 wherein the detector is adapted to identify the at least one component of the spectroscopy signal corresponding to the sample via spectral subtraction.

13. The spectrometer of claim 10 wherein the detector is adapted to identify the at least one component of the spectroscopy signal corresponding to the sample via spectral subtraction of at least one known component.

14. The spectrometer of claim 10 wherein the detector is adapted to identify the at least one component of the spectroscopy signal corresponding to the sample via spectral subtraction of at least one known component stored in a library.

15. The spectrometer of claim 14 wherein the library stores spectral interference components of a plurality of known materials.

16. The spectrometer of claim 14 wherein the plurality of known materials includes a plurality of containers.

17. The spectrometer of claim 14 wherein the plurality of known materials includes a plurality of plastic containers.

18. A method of measuring Raman scattering from layers within a sample comprising:
    exciting Raman scattering at a nonzero angle relative to a normal angle of incidence relative to the sample via an excitation incident beam directed at an entry region of the sample offset from a collection region of the sample;
    using multiple angles to interrogate the different depths corresponding to different layers within the sample;
    collecting Raman spectra at the normal angle of incidence to the surface; and
    using statistical methods to derive the different layers within the sample.

19. A method of measuring Raman scattering from layers within a sample comprising:
    exciting Raman scattering by directing an excitation beam toward an entry region of the sample at a nonzero angle relative to a normal angle of incidence relative to the sample, wherein the entry region is offset from a collection region of the sample;
    translating the using multiple angles to interrogate the different depths corresponding to different layers within the sample;
    collecting Raman spectra at normal incidence to the surface; and
    using statistical methods to derive the different layers within the sample.

20. The method of claim 19 wherein the operation of translating comprises translating a mirror along a translation axis to direct the excitation beam at the nonzero angle toward the sample from a plurality of locations.

21. A method of measuring Raman scattering from layers within a sample comprising:
    exciting Raman scattering at a nonzero angle relative to a normal angle of incidence relative to the sample via an excitation incident beam directed at an entry region of the sample offset from a collection region of the sample;
    collecting Raman spectra at the normal angle of incidence to the surface;
    collecting a spectrum of a first layer without ingredients;
    collecting a spectrum of the first layer and a second layer; and
    determining a spectrum of the second layer through normalization against the spectrum of the first layer.

* * * * *